(12) United States Patent
Okada et al.

(10) Patent No.: US 11,366,097 B2
(45) Date of Patent: Jun. 21, 2022

(54) CELL IMAGING METHOD, CELL IMAGING APPARATUS, PARTICLE IMAGING METHOD, AND PARTICLE IMAGING APPARATUS

(71) Applicant: SYSMEX CORPORATION, Kobe (JP)

(72) Inventors: Masaya Okada, Kobe (JP); Shigeki Iwanaga, Kobe (JP)

(73) Assignee: SYSMEX CORPORATION, Hyogo (JP)

(*) Notice: Subject to any disclaimer, the term of this patent is extended or adjusted under 35 U.S.C. 154(b) by 0 days.

(21) Appl. No.: 15/883,329

(22) Filed: Jan. 30, 2018

(65) Prior Publication Data
US 2019/0033291 A1 Jan. 31, 2019

(30) Foreign Application Priority Data

Jul. 31, 2017 (JP) .............................. JP2017-147660

(51) Int. Cl.
G01N 33/49 (2006.01)
G01N 15/14 (2006.01)
(Continued)

(52) U.S. Cl.
CPC .......... G01N 33/4915 (2013.01); C12Q 1/68 (2013.01); G01N 1/10 (2013.01); G01N 15/1404 (2013.01); G01N 15/147 (2013.01); G01N 15/1436 (2013.01); G01N 21/17 (2013.01); G01N 33/48728 (2013.01); G01N 33/5044 (2013.01);
(Continued)

(58) Field of Classification Search
CPC ........ G02B 21/004; G02B 21/33; A61B 1/00; G01N 33/4915; G01N 21/17; G01N 33/48728; G01N 33/5044; G01N 2015/1006; G01N 2015/144; G01N 2015/1454; C12Q 1/68
See application file for complete search history.

(56) References Cited

U.S. PATENT DOCUMENTS 8,935,107 B1 * 1/2015 Adamovsky .............. G01F 1/74
702/50
2003/0133096 A1 * 7/2003 Aroussi ................... A61B 5/027
356/28
(Continued)

FOREIGN PATENT DOCUMENTS

CN 104407436 A 3/2015
JP 2008-215999 A 9/2008
(Continued)

OTHER PUBLICATIONS

The Japanese Office Action dated Apr. 13, 2021 in a counterpart Japanese patent application No. 2017-147660.

Primary Examiner — Jefferey F Harold
Assistant Examiner — Timothy R Newlin
(74) Attorney, Agent, or Firm — Crowell & Moring LLP

(57) ABSTRACT

Disclosed is a cell imaging method including: forming a light sheet with respect to a flow cell; causing a measurement sample containing a plurality of cells to flow in the flow cell; and receiving lights generated from the plurality of cells passing through the light sheet, by an imaging device via an element configured to extend a depth of focus, and taking images of the plurality of cells by the imaging device.

15 Claims, 20 Drawing Sheets

(51) Int. Cl.

| | | |
|---|---|---|
| *G01N 1/10* | (2006.01) | |
| *C12Q 1/68* | (2018.01) | |
| *G01N 33/487* | (2006.01) | |
| *G01N 33/50* | (2006.01) | |
| *G01N 21/17* | (2006.01) | |
| *G01N 15/10* | (2006.01) | |

(52) U.S. Cl.
CPC ............... *G01N 2015/1006* (2013.01); *G01N 2015/144* (2013.01); *G01N 2015/1454* (2013.01)

(56) References Cited

U.S. PATENT DOCUMENTS

| | | | | |
|---|---|---|---|---|
| 2004/0104681 A1* | 6/2004 | Mitrovic | ............ | G01N 15/0227 315/111.21 |
| 2009/0231660 A1* | 9/2009 | Huang | ................ | G02B 26/125 359/226.1 |
| 2010/0278400 A1* | 11/2010 | Piestun | .............. | G01N 21/6456 382/128 |
| 2011/0249866 A1* | 10/2011 | Piestun | ................ | H04N 13/204 382/103 |
| 2011/0310226 A1* | 12/2011 | McEldowney | .... | G01B 11/2513 348/46 |
| 2013/0147925 A1* | 6/2013 | Lew | .................... | H04N 13/204 348/49 |
| 2013/0302905 A1* | 11/2013 | Kalkbrenner | ...... | G01N 21/6428 436/172 |
| 2014/0099659 A1* | 4/2014 | Keller | ................ | G01N 21/6486 435/29 |
| 2014/0239073 A1 | 8/2014 | Toyoda et al. | | |
| 2014/0254005 A1* | 9/2014 | Lippert | ................ | G02B 21/367 359/385 |
| 2014/0340483 A1* | 11/2014 | Ritter | .................. | G01N 21/6458 348/46 |
| 2014/0346328 A1* | 11/2014 | Niu | ...................... | G02B 5/1842 250/225 |
| 2014/0353522 A1 | 12/2014 | Wu et al. | | |
| 2015/0022881 A1 | 1/2015 | Loza Alvarez et al. | | |
| 2015/0177065 A1* | 6/2015 | Wu | .................... | G01N 15/0211 356/402 |
| 2015/0192510 A1 | 7/2015 | Piestun et al. | | |
| 2015/0379695 A1* | 12/2015 | Naruse | .................. | H04N 1/409 348/234 |
| 2016/0048963 A1* | 2/2016 | Piestun | ................ | G06K 9/6807 382/154 |
| 2016/0125610 A1* | 5/2016 | Piestun | ................ | H04N 13/204 348/46 |
| 2016/0327779 A1* | 11/2016 | Hillman | ............... | G02B 21/367 |
| 2016/0370570 A1 | 12/2016 | Foelling | | |
| 2017/0082531 A1 | 3/2017 | Okada et al. | | |
| 2018/0074305 A1* | 3/2018 | Atzler | ................ | G01N 21/6458 |
| 2019/0196167 A1* | 6/2019 | Maddox | ............ | G02B 21/0032 |
| 2019/0204580 A1* | 7/2019 | Fahrbach | ............ | G02B 21/0032 |

FOREIGN PATENT DOCUMENTS

| | | |
|---|---|---|
| JP | 2014-164721 A | 9/2014 |
| JP | 2014-224814 A | 12/2014 |
| JP | 2016-507078 A | 3/2016 |
| JP | 2016-525225 A | 8/2016 |
| JP | 2017-15742 A | 1/2017 |
| JP | 2017-504836 A | 2/2017 |
| JP | 2017-58352 A | 3/2017 |
| WO | 2014/117079 A1 | 7/2014 |
| WO | 2015/109323 A2 | 7/2015 |

* cited by examiner

FARTHEST POSITION

INTERMEDIATE POSITION

CLOSEST POSITION

| PIXEL LINE | X CORRECTION VALUE | Z CORRECTION VALUE |
|---|---|---|
| PL1 | Xa1 | Za1 |
| PL2 | Xa2 | Za2 |
| ⋮ | ⋮ | ⋮ |
| PLn | Xan | Zan |

CELL IMAGING METHOD, CELL IMAGING APPARATUS, PARTICLE IMAGING METHOD, AND PARTICLE IMAGING APPARATUS

RELATED APPLICATIONS

This application claims priority from prior Japanese Patent Application No. 2017-147660, filed on Jul. 31, 2017, entitled "CELL IMAGING METHOD, CELL IMAGING APPARATUS, PARTICLE IMAGING METHOD, AND PARTICLE IMAGING APPARATUS", the entire content of which is incorporated herein by reference.

BACKGROUND OF THE INVENTION

1. Field of the Invention

The present invention relates to a cell imaging method, a cell imaging apparatus, a particle imaging method, and a particle imaging apparatus.

2. Description of the Related Art

Japanese Laid-Open Patent Publication No. 2017-58352 discloses a particle imaging apparatus capable of taking cross-sectional images of particles by inclining a sheet surface of a light sheet with respect to a flow of a sample that flows in a flow cell. That is, as shown in FIGS. 20A and 20B, a particle imaging apparatus 300 includes: a light source 301, an irradiation optical system 302, a flow cell 303, a condensing optical system 304, and an imaging device 305. Light emitted from the light source 301 is converged by the irradiation optical system 302, thereby forming a light sheet 310. A sheet surface of the light sheet 310 is perpendicular to an outer side surface 303a of the flow cell 303, and is inclined at a predetermined angle with respect to a flow direction of a sample that flows in the flow cell 303. Fluorescence generated from a particle 320 is condensed onto an imaging surface 305a of the imaging device 305 by the condensing optical system 304 including an object lens 304a.

When cells are imaged, it is desirable to improve throughput so that as many cell images as possible per unit time can be obtained. Demand for improved throughput is particularly high when images of rare cells contained in a sample are taken. In this case, by simultaneously imaging a plurality of cells that simultaneously cross a light sheet, the number of cell images obtainable per unit time can be increased. In this case, however, the taken image of a cell that flows at a position that significantly deviates from a focal position of an object lens becomes unclear due to focus deviation.

When culture stem cells are evaluated, it is useful to image and analyze an aggregate resulting from aggregation of a plurality of cells. In this case, since such an aggregate is larger than a single cell, the aggregate has a relatively large width in the optical axis direction of the object lens. Therefore, a portion of the aggregate may significantly deviate from the focal position of the object lens, and a portion, of the taken image, corresponding to this portion of the aggregate may become unclear.

SUMMARY OF THE INVENTION

The scope of the present invention is defined solely by the appended claims, and is not affected to any degree by the statements within this summary.

A first aspect of the present invention provides a cell imaging method. The cell imaging method according to this aspect includes: forming a light sheet (11) with respect to a flow cell (40) (S11); causing a measurement sample containing a plurality of cells to flow in the flow cell (40) (S12); receiving lights generated from the plurality of cells passing through the light sheet (11), by an imaging device (60) via an element (55) configured to extend a depth of focus (S13), and taking images of the plurality of cells by the imaging device (60) (S14).

The "depth of focus" is a range of distance on a measurement target side, in which an image taken by the imaging device appears to be in focus, in an optical axis direction of a condensing optical system.

According to the cell imaging method of this aspect, the lights generated from the plurality of cells flowing in the flow cell are imaged via the element configured to extend the depth of focus. Therefore, clear cross-sectional images of the cells can be obtained regardless of the positions of the cells flowing in the flow cell. Accordingly, a high-quality image including the plurality of cells can be generated.

In the cell imaging method of this aspect, the light sheet (11) may be formed to be inclined such that the light sheet (11) is not perpendicular to a flow direction of the sample. Thus, the lights generated from the plurality of cells can be imaged from the side of the flow cell (40).

In the cell imaging method of this aspect, the plurality of cells are caused to simultaneously pass through the light sheet (11), and lights generated from the plurality of cells are received by the imaging device (60). Thus, the images of the plurality of cells can be simultaneously taken, thereby obtaining an image including the cross-sectional images of the plurality of cells.

In the cell imaging method of this aspect, the element (55) configured to extend the depth of focus may be a phase modulation element (55) configured to modulate a point spread function.

In this case, the point spread function may be a spiral point spread function. Thereby, the depth of focus can be effectively extended.

The "spiral point spread function" is a point spread function that allows light generated from one bright point to be imaged onto a rotational position on an image surface corresponding to a depth position of the bright point.

The point spread function may be a single-helix point spread function. In this case, since lights generated from portions at the cross section of each cell are not separated, an excellent taken image can be obtained.

The "single-helix point spread function" is a kind of a spiral point spread function, and is a point spread function that allows light generated from one bright point to be imaged on one focal point.

The cell imaging method of this aspect may include subjecting an image including taken images of the plurality of cells to correction of distortion of each taken image, the distortion being caused by the phase modulation element (55) (S21). By correcting distortion, of the taken image, caused by the effect of the phase modulation element, a high quality cell image can be obtained.

For example, in the correcting of the distortion of the taken image (S21), image elements forming the taken image are each shifted to a position at which displacement thereof based on the point spread function is corrected. By individually shifting the image elements, distortion of the entire taken image can be appropriately corrected.

Specifically, in the correcting of the distortion of the taken image (S21), each image element is shifted on the basis of a distance between the light sheet (11) and a position, on an imaging surface (61), at which the image element is obtained. Thus, distortion of the taken image can be appropriately corrected.

More specifically, in the correcting of the distortion of the taken image (S21), each image element is shifted in a direction and by a distance, the direction and the distance being based on the distance between the light sheet (11) and the position, on the imaging surface (61), at which the image element is obtained. Thus, distortion of the taken image can be appropriately corrected by a simple process.

In this case, each image element may be an image element obtained pixel by pixel. Thus, by setting each image element to be corrected, to an image element obtained from each pixel that is the minimum unit of imaging, distortion of the taken image can be corrected with high accuracy.

Each "image element" is an image portion included in each unit block when a taken image is divided into predetermined unit blocks. Each image element may be an image portion corresponding to one pixel as described above, or may be an image portion included in a unit block composed of a predetermined number of pixels in each of up and down directions.

Further, in the correcting of the distortion of the taken image (S21), the image elements obtained from pixel lines (PL1 to PLn) having the same distance from the light sheet (11) may be shifted in a direction and by a distance, the direction and the distance being based on the distance between the pixel lines (PL1 to PLn) and the light sheet (11). Thus, distortion of the taken image can be appropriately corrected by a very simple process.

In the cell imaging method of this aspect, a plurality of images each including a plurality of cells are taken, and an image including three-dimensional images of the plurality of cells is generated on the basis of the plurality of taken images. Thus, high-quality three-dimensional images of the plurality of cells can be obtained.

In the cell imaging method of this aspect, the generating of the image (S15) includes correcting a position of the image of each cell at the imaging surface (61) (S23). In the correcting of the position (S23), an amount of shifting of the image of the cell on the imaging surface (61) may be calculated on the basis of, at least, an amount of movement of the cell in the flow cell (40), and an angle of the light sheet (11) with respect to the flow direction of the sample, and the three-dimensional image of the cell may be generated on the basis of the calculated amount of shifting, and a series of the taken images obtained along with movement of the cell. Thus, by generating the three-dimensional images of the plurality of cells in consideration of the amount of shifting of the image at the imaging surface, higher-quality three-dimensional images can be obtained.

Further, the generating of the image (S21) includes correcting a size of the image of each cell on the imaging surface (61) (S22). In the correcting of the size (S22), the size of the taken image of the cell is corrected on the basis of an angle of the light sheet (11) with respect to the flow direction of the sample, and the three-dimensional image of the cell is generated on the basis of the size-corrected image. Thus, by correcting the size of the taken image, a higher-quality three-dimensional image can be obtained.

A second aspect of the present invention provides a cell imaging apparatus. The cell imaging apparatus according to this aspect includes: a flow cell (40) configured to cause a sample containing a plurality of cells to flow therein; a light source (20); an irradiation optical system (30) configured to form, with respect to the flow cell (40), a light sheet (11) from light emitted from the light source (20); a condensing optical system (50) having an element (55) configured to extend a depth of focus, the condensing optical system (50) being configured to condense lights generated from the plurality of cells flowing in the flow cell (40); and an imaging device (60) configured to receive lights that have been generated from the plurality of cells and condensed by the condensing optical system (50), and take images of the plurality of cells.

According to the cell imaging device of this aspect, the lights generated from the plurality of cells flowing in the flow cell are imaged via the element configured to extend the depth of focus. Therefore, clear cross-sectional images of the cells can be obtained regardless of the positions of the cells flowing in the flow cell. Accordingly, a high-quality image including the plurality of cells can be generated.

In the cell imaging apparatus of this aspect, the element (55) configured to extend the depth of focus may be a phase modulation element (55) configured to modulate a point spread function.

In this case, the phase modulation element (55) may be configured to form a spiral point spread function at an imaging surface (61) of the imaging device (60). Thus, the depth of focus can be effectively extended.

The spiral point spread function may be a single-helix point spread function. In this case, since lights generated from portions at the cross section of each cell are not separated, an excellent taken image can be obtained.

The cell imaging apparatus of this aspect may include a processing section (81) configured to process the images taken by the imaging device (60). The processing section (81) may be configured to execute a process of correcting distortion of each taken image, the distortion being caused by the phase modulation element (55), and generate an image including the plurality of cells on the basis of the distortion-corrected taken images. By correcting distortion, of the taken image, caused by the effect of the phase modulation element, a high quality cell image can be obtained.

For example, the processing section (81) may be configured to cause each of image elements forming the taken image to shift to a position at which displacement of the image element based on the point spread function is corrected, thereby correcting the distortion of the taken image. By individually shifting the image elements, distortion of the entire taken image can be appropriately corrected.

Specifically, the processing section (81) may be configured to cause each of the image elements forming the taken image to shift, on the basis a distance between the light sheet (11) and a position, on an imaging surface (61), at which the image element is obtained, thereby correcting the distortion of the taken image. Thus, distortion of the taken image can be appropriately corrected.

More specifically, the processing section (81) may be configured to cause the image element to shift in a direction and by a distance, the direction and the distance being based on the distance between the light sheet (11) and the position, on the imaging surface (61), at which the image element is obtained, thereby correcting the distortion of the taken image. Thus, distortion of the taken image can be appropriately corrected by a simple process.

In this case, each image element may be an image element obtained for each of pixels of the imaging device (60). Thus, by setting each image element to be corrected, to an image element obtained from each pixel that is the minimum unit of imaging, distortion of the taken image can be corrected with high accuracy.

The processing section (81) may be configured to cause the image elements obtained from pixel lines (PL1 to PLn) having the same distance from the light sheet (11), to shift in a direction and by a distance, the direction and the distance being based on the distance between the pixel lines (PL1 to PLn) and the light sheet (11), thereby correcting the distortion of the taken image. Thus, distortion of the taken image can be appropriately corrected by a very simple process.

Further, the point spread function may be a multi-helix point spread function. In this case, the processing section (81) may be configured to cause a plurality of image elements that are paired based on the point spread function to shift to an intermediate position between these image elements, thereby correcting the distortion of the taken image. Thus, by superposing the plurality of image elements that are paired, a bright taken image can be generated.

The "multi-helix point spread function" is a kind of a spiral point spread function, and is a point spread function that allows light generated from one bright point to be imaged on a plurality of focal points.

In the cell imaging apparatus of this aspect, the phase modulation element (55) may be a spatial light modulator, a deformable mirror, or a phase plate.

In the cell imaging apparatus of this aspect, the processing section (81) may be configured to generate an image including three-dimensional images of the plurality of cells, on the basis of the taken images. Thus, high-quality three-dimensional images of the plurality of cells can be obtained.

In this case, the processing section (81) may be configured to calculate an amount of shifting of the image of each cell on an imaging surface (61) of the imaging device (60), on the basis of, at least, an amount of movement of the cell in the flow cell (40), and an angle of the light sheet (11) with respect to the flow direction of the sample, and generate the three-dimensional image of the cell on the basis of the calculated amount of shifting, and a series of the taken images obtained along with movement of the cell. Thus, by generating the three-dimensional images of the plurality of cells in consideration of the amount of shifting of the image at the imaging surface, higher-quality three-dimensional images can be obtained.

Further, the processing section (81) may be configured to correct a size of each taken image on the basis of an angle of the light sheet (11) with respect to the flow direction of the sample, and generate the three-dimensional images of the plurality of cells on the basis of the size-corrected images. Thus, by correcting the size of each taken image, a higher-quality three-dimensional image can be obtained.

The sheet surface (11*a*) of the light sheet (11) may be perpendicular to an outer side surface (40*a*) of the flow cell (40). Thus, light incident on the flow cell is inhibited from being deflected by the flow cell, whereby the shape of the beam that passes through the flow cell and is applied to a cell is less likely to be deformed. Accordingly, the light sheet having an appropriate shape can be applied to the cell, whereby a high-definition image can be taken.

The optical axis of the condensing optical system (50) may be perpendicular to the flow direction of the sample. Thus, the imaging device receives light that goes out of the flow cell without being substantially deflected by the flow cell, whereby the beam shape of the light applied to the imaging surface is less likely to be deformed. Therefore, a high-definition image can be imaged by the imaging device.

The optical axis of the irradiation optical system (30) and the optical axis of the condensing optical system (50) may be perpendicular to each other. Thus, the imaging device can image light emitted from the cross section of each cell, from the front side. In this case, a process of correcting the taken image in the direction perpendicular to the flow of the sample need not be performed.

The irradiation optical system (30) may be configured to include: an optical lens (31) configured to converge the light emitted from the light source (20) such that convergence of the light in a first direction (D1) is different from convergence of the light in a second direction (D2) that crosses the first direction (D1); and a rotation mechanism section (32) configured to rotate the optical lens (31) about an optical axis of the irradiation optical system (30) in the optical lens (31). In this configuration, by adjusting the rotation angle of the optical lens, a high-definition image with reduced background noise can be taken while satisfactorily obtaining a series of cross-sectional images of each cell.

A third aspect of the present invention provides a particle imaging method. The particle imaging method according to this aspect includes: forming a light sheet (11) with respect to a flow cell (40) (S11); taking an image of light generated from a particle that flows in the flow cell (40), via a phase modulation element (55) configured to modulate a point spread function (S13); and correcting distortion of the taken image, the distortion being caused by the phase modulation element (55) (S21).

According to the particle imaging method of this aspect, since the condensing optical system includes the phase modulation element, the depth of focus of the condensing optical system can be extended, whereby a clear cross-sectional image of the particle can be obtained regardless of the position of particle in the optical axis direction of the condensing optical system. Further, since distortion, of the taken image, caused by the effect of the phase modulation element is corrected by a processing section, a high-quality particle image can be obtained. Thus, according to the particle imaging method of this aspect, a higher-quality particle image can be generated regardless of the position of the particle flowing in the flow cell.

A fourth aspect of the present invention provides a particle imaging apparatus. The particle imaging apparatus according to this aspect includes: a flow cell (40) configured to cause a sample containing a particle to flow therein; a light source (20); an irradiation optical system (30) configured to form, with respect to the flow cell (40), a light sheet (11) from light emitted from the light source (20); a condensing optical system (50) having a phase modulation element (55) configured to extend a depth of focus, the condensing optical system (50) being configured to condense light generated from the particle that flows in the flow cell (40); an imaging device (60) configured to receive the light condensed by the condensing optical system (50); and a processing section (81) configured to correct distortion of the image taken by the imaging device (60).

According to the particle imaging apparatus of this aspect, the same effects achieved by the third aspect can be achieved.

DETAILED DESCRIPTION OF THE PREFERRED EMBODIMENTS

Embodiment 1

Embodiment 1 is a cell imaging apparatus configured to image fluorescences generated from a cell that is irradiated with light, thereby obtaining a plurality of images, and configured to generate a three-dimensional image of the cell on the basis of the obtained plurality of images. Examples of the imaging target cell include: a circulating tumor cell (CTC); a circulating endothelial cell (CEC); an endothelial progenitor cell (EPC); an mesenchymal stem cell (MSC); a hematopoietic stem cell (HSC); and an antigen-specific T-cell.

In Embodiment 1, a fluorescence image of a nucleus in the imaging target cell is obtained.

Figure 1:
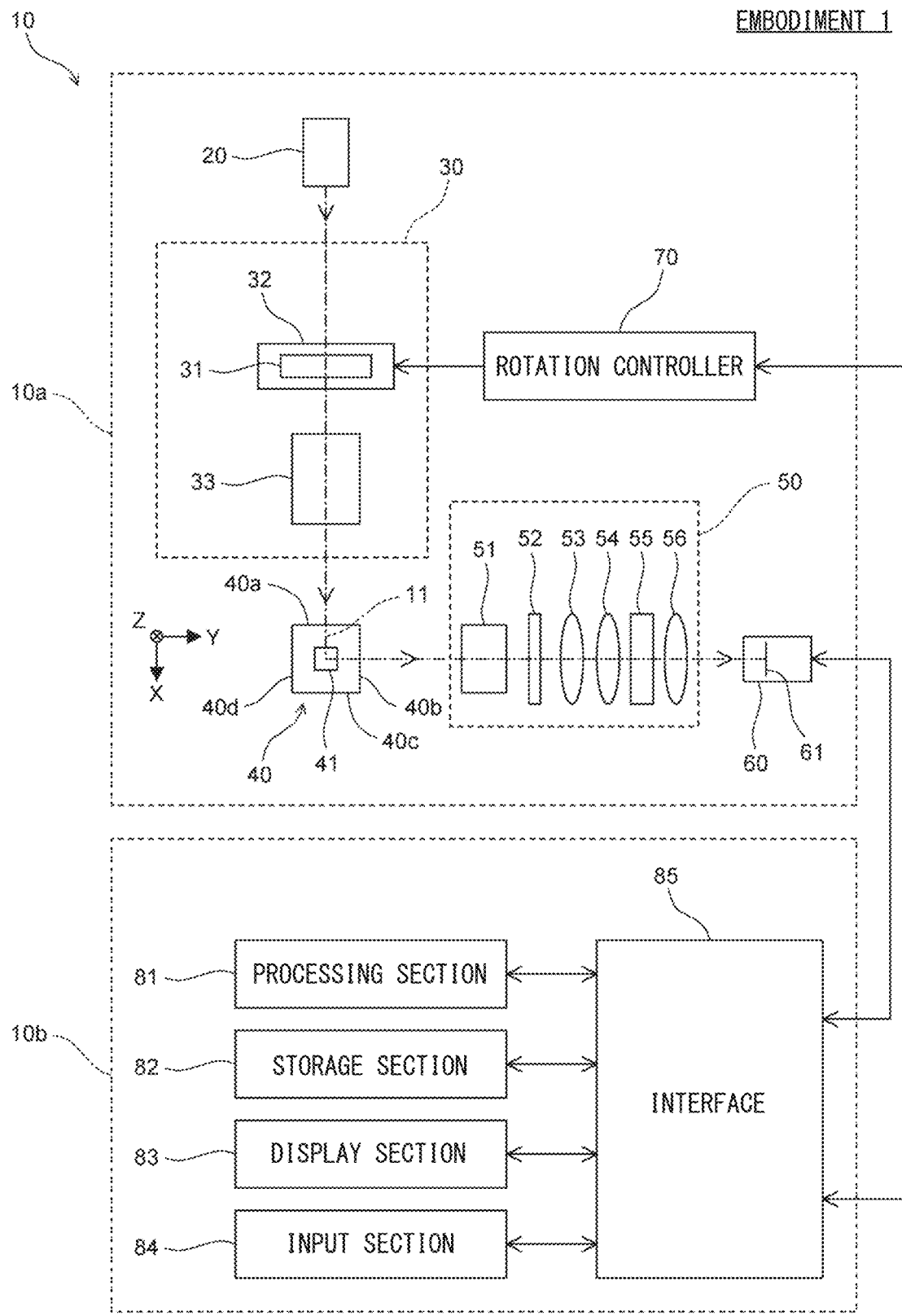
FIG. 1 is a diagram showing a configuration of a cell imaging apparatus according to Embodiment 1.

As shown in FIG. 1, a cell imaging apparatus 10 includes an imaging unit 10a and an information processing unit 10b. The imaging unit 10a includes a light source 20, an irradiation optical system 30, a flow cell 40, a condensing optical system 50, an imaging device 60, and a rotation controller 70. In FIG. 1, XYZ axes are shown for the purpose of explaining arrangement of the respective components of the imaging unit 10a. The XYZ axes are orthogonal to each other. XYZ axes shown in the following drawings correspond to the XYZ axes shown in FIG. 1.

The irradiation optical system 30 includes an optical lens 31, a rotation mechanism section 32, and an object lens 33. The condensing optical system 50 includes an object lens 51, an optical filter 52, condenser lenses 53, 54, and 56, and a phase modulation element 55. In this embodiment, a transmission type phase modulation element 55 is assumed.

The light source 20 emits light in the X-axis positive direction to irradiate a sample flowing in the flow cell 40 with the light. The light source 20 is, for example, a semiconductor laser light source. The wavelength of the light emitted from the light source 20 is set to a wavelength of light for exciting fluorescence from a fluorescent dye that stains each cell. The optical lens 31 converges the light emitted from the light source 20 as described later. The rotation mechanism section 32 rotatably supports the optical lens 31. The rotation mechanism section 32 causes the optical lens 31 to rotate about the center axis of the light emitted from the light source 20, that is, about the optical axis of the irradiation optical system 30 in the optical lens 31.

Figure 2A:
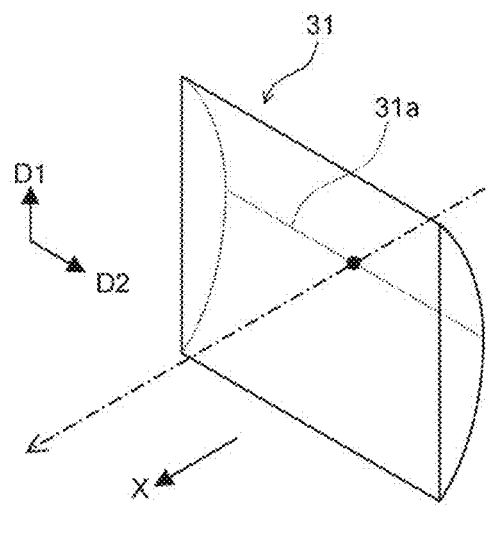
FIG. 2A is a diagram showing a configuration of an optical lens according to Embodiment 1.

As shown in FIG. 2A, the optical lens 31 is a cylindrical lens. The X-axis positive side of the optical lens 31 is a flat surface, while the X-axis negative side of the optical lens 31 is a curved surface. The optical lens 31 is supported by the rotation mechanism section 32 such that the X-axis positive side surface thereof is perpendicular to the X-axis, and the center axis of the light incident on the optical lens 31 crosses a generatrix 31a of the optical lens 31. The optical lens 31 is preferably arranged such that the flat surface thereof is positioned on the X-axis positive side while the curved surface thereof is positioned on the X-axis negative side as described above. However, the optical lens 31 may be arranged such that the curved surface is positioned on the X-axis positive side while the flat surface is positioned on the X-axis negative side.

The optical lens 31 converges the light emitted from the light source 20 such that convergence of the light in the first direction D1 is different from convergence of the light in a second direction D2 that crosses the first direction D1. Specifically, the first direction D1 is a direction perpendicular to the generatrix 31a and the X-axis, and the second direction D2 is a direction parallel to the generatrix 31a. The optical lens 31 does not converge the light emitted from the light source 20 in the second direction D2, but converges the light only in the first direction D1. The light converged in the first direction D1 by the optical lens 31 is condensed on and around a pupil of the object lens 33.

Figure 2B:
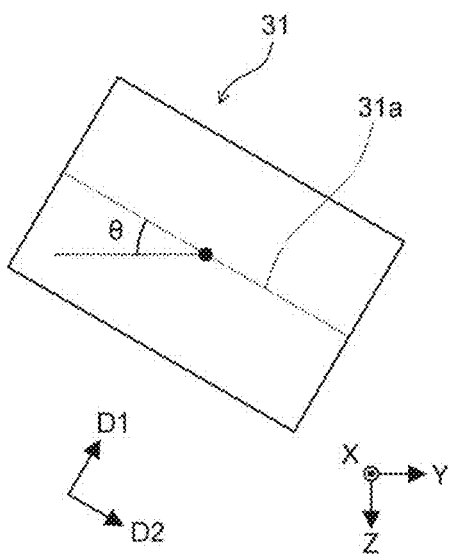
FIG. 2B is a diagram showing a state in which the optical lens according to Embodiment 1 is inclined.

As shown in FIG. 2B, the optical lens 31 is rotated about the X-axis by the rotation mechanism section 32, and is located at a rotational position at which the angle of the generatrix 31a with respect to the Y-axis is a predetermined angle θ. Thus, the optical lens 31 converges the light emitted from the light source 20 only in the first direction D1 inclined with respect to the Z-axis as shown in FIG. 2B.

Referring back to FIG. 1, the object lens 33 causes the light transmitted through the optical lens 31 to be condensed onto a flow path 41 of the flow cell 40. Specifically, the object lens 33 converges the light transmitted through the optical lens 31 such that the convergence position of the light in the second direction D2 shown in FIG. 2B is positioned in the flow path 41 of the flow cell 40. In addition, the object lens 33 collimates the light transmitted through the optical lens 31, in the first direction D1 shown in FIG. 2B. Thus, the light transmitted through the object lens 33 becomes a flat beam in the flow path 41 of the flow cell 40.

The object lens 33 may be omitted. In this case, the optical lens 31, being in the state shown in FIG. 2B, is rotated by 90° about the X-axis. Then, the light emitted from the light source 20 is converged by the optical lens 31 only in one direction, whereby a flat beam is formed in the flow path 41 of the flow cell 40.

As described above, the irradiation optical system 30, by means of the optical lens 31 and the object lens 33, causes the light emitted from the light source 20 to be linearly condensed onto a cross section parallel to the YZ plane at the position of the flow path 41 of the flow cell 40. That is, the irradiation optical system 30 forms a light sheet 11 with respect to the flow cell 40, from the light emitted from the light source 20.

The optical lens 31 may be a lens that causes convergence of the light in the first direction D1 to be different from convergence of the light in the second direction D2. The optical lens 31 may be a phase plate or a holography element. The irradiation optical system 30 may form the light sheet 11 by forming a Bessel beam by using a conical lens or the like, and scanning the formed Bessel beam at a high speed in one direction by using a scanning mirror or the like. In this case, the scanning direction of the scanning mirror or the like is, in the YZ plane, a direction other than the Y-axis direction and the Z-axis direction.

The flow cell 40 has a shape extending in the Z-axis direction, and has a cross section of a square outer shape as viewed in the Z-axis direction. The flow cell 40 may have a cross section of an outer shape that is a rectangle other than a square as viewed in the Z-axis direction. Outer side surfaces 40a, 40b, 40c, and 40d of the flow cell 40 are flat surfaces. In particular, the outer side surface 40a on which the light from the irradiation optical system 30 is incident, and the outer side surface 40b through which fluorescence condensed by the condensing optical system 50 described later passes, are desired to be flat surfaces. In Embodiment 1, the outer side surface 40c of the flow cell 40 on the X-axis positive side and the outer side surface 40a of the flow cell 40 on the X-axis negative side, are parallel to the YZ plane, while the outer side surface 40b of the flow cell 40 on the Y-axis positive side and the outer side surface 40d of the flow cell 40 on the Y-axis negative side, are parallel to the XZ plane.

The flow path 41 extending in the Z-axis direction is formed in the flow cell 40. The flow cell 40 causes a sample containing cells to flow in the flow path 41. The sample that flows in the flow path 41 has been prepared in advance on the basis of cells collected from a subject. In Embodiment 1, when the sample is prepared, nuclei in the cells are fluorescently stained. The nuclei are stained by fluorescent dyes that can specifically stain the nuclei. The dyes that stain the nuclei cause excitation of fluorescences having different wavelengths when being irradiated with the light emitted from the light source 20. When cells that intrinsically generate fluorescences are to be imaged, these cells are not necessarily fluorescently stained.

Figure 2C:
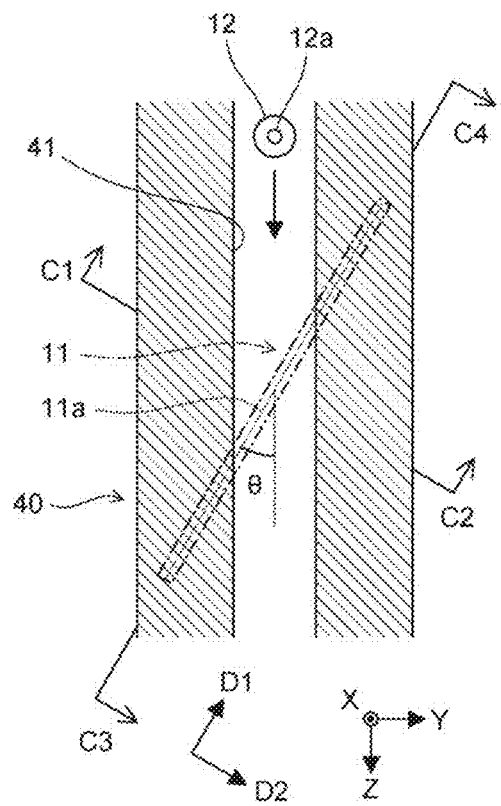
FIG. 2C is a schematic diagram in which the cross sections of a flow cell and a light sheet in a flow path according to Embodiment 1 are viewed in an X-axis negative direction.

As shown in FIG. 2C, when the flow path 41 is viewed in the X-axis negative direction, the longitudinal direction of the light sheet 11 is not perpendicular to the sample flow direction but is inclined at a predetermined angle. That is, the light sheet 11 has a shape extending in the first direction D1 and having a narrow width in the second direction D2. The light sheet 11 is schematically shown by a long chain line. Each cell 12 contained in the sample flows in the Z-axis positive direction in the flow path 41 of the flow cell 40. At this time, a nucleus 12a in the cell 12 also flows in the Z-axis positive direction in the flow path 41. When the cell 12 crosses the light sheet 11, fluorescence is generated from a fluorescently stained portion of the cell 12.

Figure 2D:
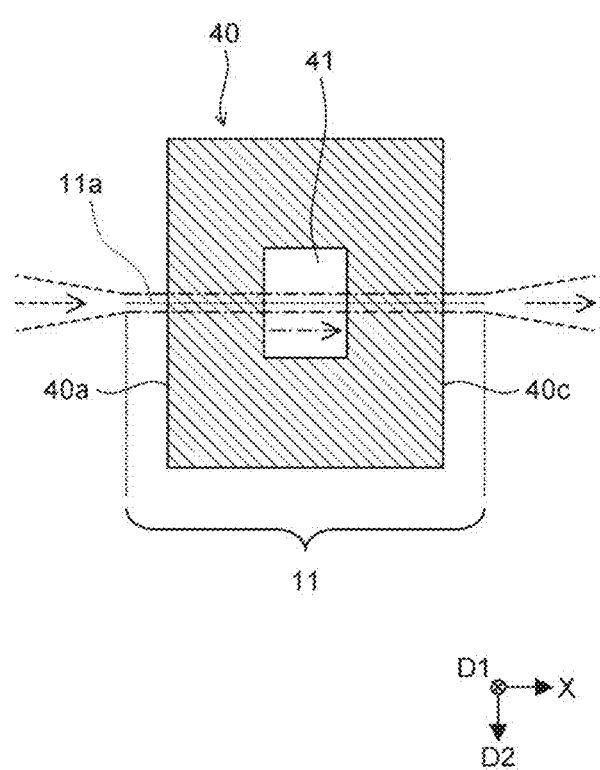
FIG. 2D is a schematic diagram in which the cross sections of the light sheet and the flow cell according to Embodiment 1 are viewed in a first direction.

When a cross section C1-C2 in FIG. 2C is viewed in the first direction D1, the cross section is as shown in FIG. 2D. As shown in FIG. 2D, the light incident on the flow cell 40 from the irradiation optical system 30 is, in the flow cell 40, parallel light whose width in the first direction D1 is not narrowed, but the width thereof in the second direction D2 is narrowed and thinned. The light sheet 11 is a region, of the light emitted from the light source 20, whose width in the second direction D2 is sufficiently narrow relative to the cell.

A sheet surface 11a of the light sheet 11 is a plane, in the light sheet 11, defined by the center axis of the light sheet 11 and the first direction D1. In FIGS. 2C and 2D, the sheet surface 11a is schematically shown by a dotted line.

Referring back to FIG. 2C, the sheet surface 11a of the light sheet 11 is inclined by an angle θ with respect to the Z-axis, in response to inclination of the optical lens 31. The inclination of the sheet surface 11a with respect to the Z-axis is set so as not to be substantially perpendicular to the Z-axis. Thus, a cross-sectional image of the cell 12 can be easily obtained from the periphery of the flow cell 40. In addition, the sheet surface 11a is set so as not to be parallel to the Z-axis. Thus, a plurality of different cross-sectional images can be obtained for the fluorescently stained portion of the cell 12. Thus, the sheet surface 11a is not substantially perpendicular to the Z-axis direction which is the sample flow direction, but is inclined at the predetermined angle. Therefore, fluorescence generated from the fluorescent dye can be easily obtained from the periphery of the flow cell 40, and a plurality of different cell cross sections can be obtained. The angle θ can be set by rotating the optical lens 31 about the X-axis.

Figure 3A:
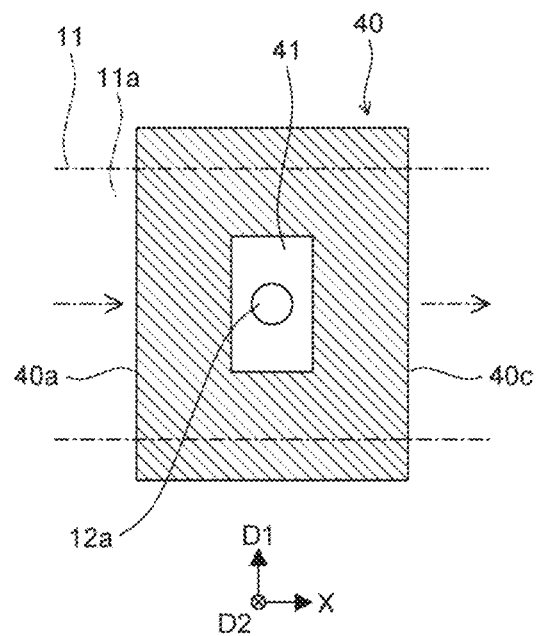
FIG. 3A is a schematic diagram in which the cross-sections of the light sheet and the flow cell according to Embodiment 1 are viewed in a second direction.

The optical axis of the irradiation optical system 30 is perpendicular to the Z-axis direction which is the sample flow direction. In other words, the optical axis of the object lens 33 is perpendicular to the Z-axis, and the central axis of the light that goes out of the irradiation optical system 30 and is incident on the flow cell 40 is perpendicular to the Z-axis. When a cross section C3-C4 shown in FIG. 2C is viewed in the second direction D2, the cross section is as shown in FIG. 3A. As shown in FIG. 3A, the sheet surface 11a of the light sheet 11 is perpendicular to the outer side surface 40a of the flow cell 40 on which the light emitted from the light source 20 is incident. Thus, the light incident on the flow cell 40 is inhibited from being deflected by the flow cell 40, whereby the shape of the beam that passes through the flow cell 40 and is applied to the nucleus 12a is less likely to be deformed. Accordingly, the light sheet 11 having an appropriate shape can be applied to the cell, thereby enabling the imaging device 60 described later to take a high-definition image.

Figure 3B:
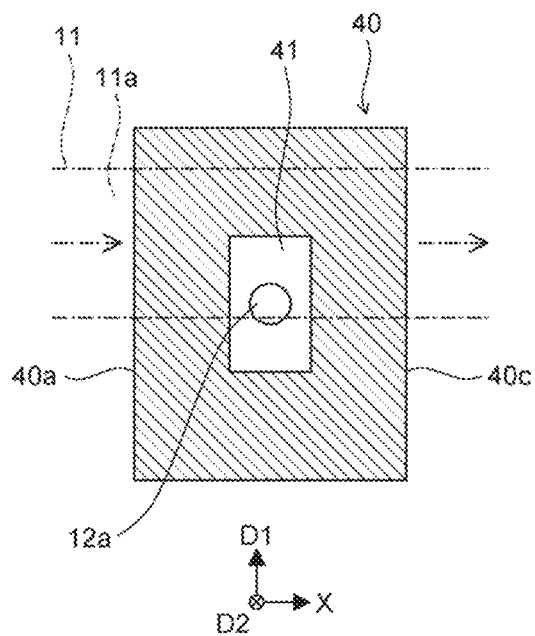
FIG. 3B is a schematic diagram in which the cross sections of the light sheet and the flow cell according to a modification of Embodiment 1 are viewed in the second direction.

When a three-dimensional image of only a portion of the nucleus 12a is required, the width of the light sheet 11 in the first direction D1 may be set such that the light sheet 11 covers only the imaging-target portion of the nucleus 12a, as shown in FIG. 3B. In this case, cross-sectional images of the portion of the nucleus 12a are obtained, and a three-dimensional image is generated on the basis of the obtained cross-sectional images of the portion of the nucleus 12a.

Figure 3C:
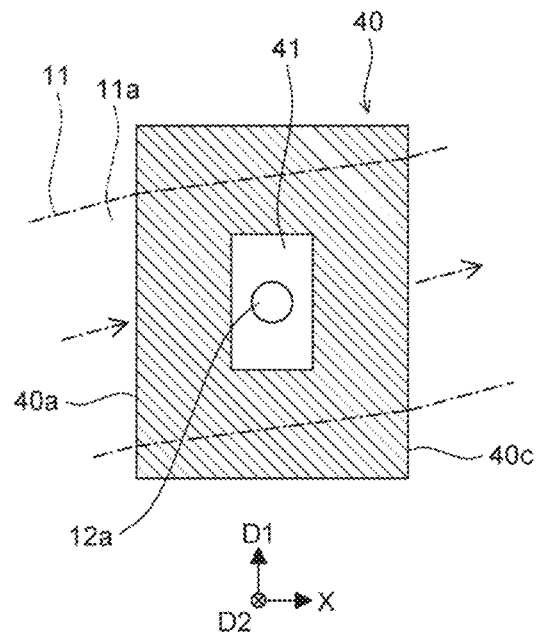
FIG. 3C is a schematic diagram in which the cross sections of the light sheet and the flow cell according to a modification of Embodiment 1 are viewed in the second direction.

The optical axis of the irradiation optical system 30 may deviate from the perpendicular state with respect to the sample flow direction. In this case, when a cross section C3-C4 shown in FIG. 2C is viewed in the second direction D2, the cross section is as shown in FIG. 3C. In FIG. 3C, the optical axis of the irradiation optical system 30 is not perpendicular to the sample flow direction, but, as in FIG. 3A, the sheet surface 11a is perpendicular to the outer side surface 40a of the flow cell 40 on which the light emitted from the light source 20 is incident. In this case, due to the outer side surface 40a, the light sheet 11 is deflected in the first direction D1, but is not deflected in the second direction D2. Accordingly, the thickness of the light sheet 11 in the second direction D2 is less likely to be affected by the outer side surface 40a of the flow cell 40. Therefore, as in the case of FIG. 3A, the shape of the beam applied to the nucleus 12a is less likely to be deformed, thereby enabling the imaging device 60 to take a high-definition image.

Figure 3D:
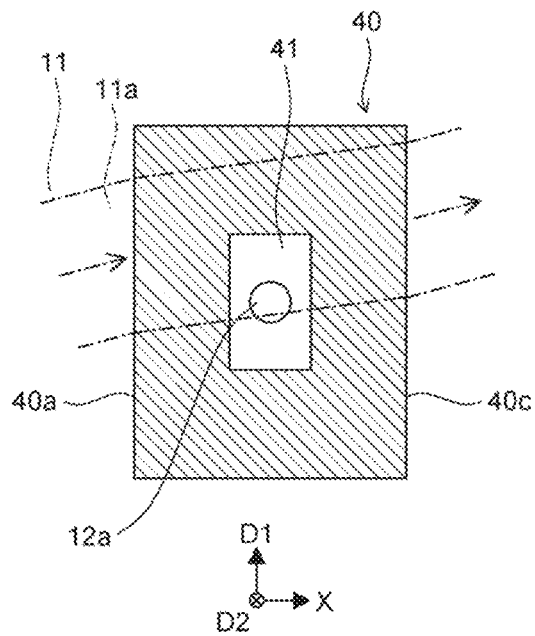
FIG. 3D is a schematic diagram in which the cross sections of the light sheet and the flow cell according to a modification of Embodiment 1 are viewed in the second direction.

When a three-dimensional image of only a portion of the nucleus 12a is required, the width of the light sheet 11 in the first direction D1 may be set such that the light sheet 11 covers only the imaging target portion of the nucleus 12a, as shown in FIG. 3D.

The sheet surface 11a may slightly deviate from the perpendicular state to the outer side surface 40a. As long as the sheet surface 11a is substantially perpendicular to the outer side surface 40a, the shape of the beam applied to the cell 12 is inhibited from being deformed, thereby enabling the imaging device 60 to take a high-definition image.

Figure 4A:
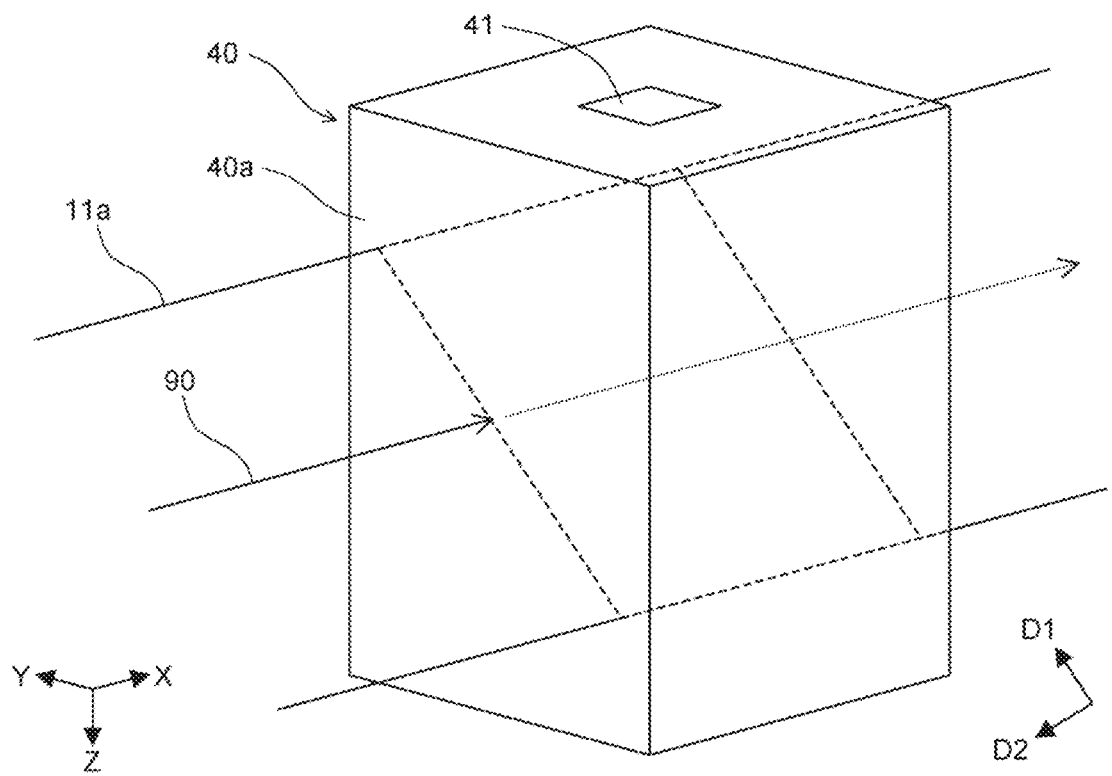
FIG. 4A is a schematic diagram showing the relationship between the sheet surface of the light sheet and the outer side surface of the flow cell according to Embodiment 1.
Figure 4B:
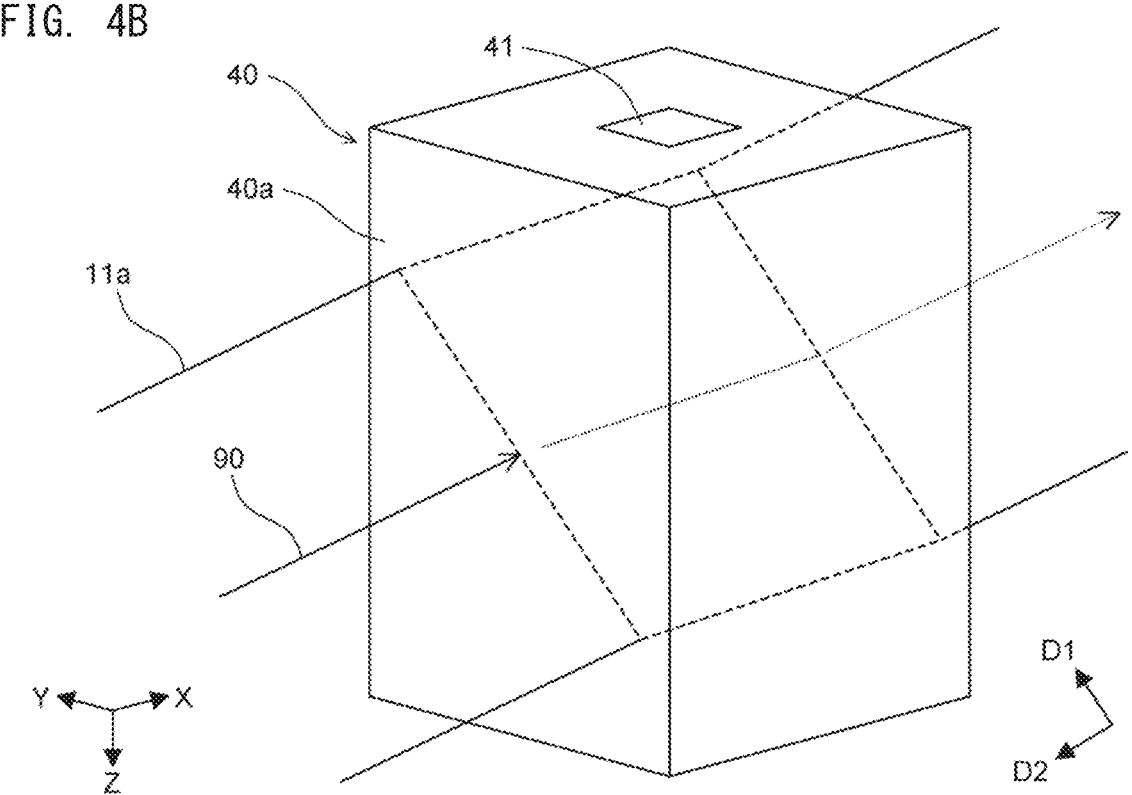
FIG. 4B is a schematic diagram showing the relationship between the sheet surface of the light sheet and the outer side surface of the flow cell according to a modification of Embodiment 1.

The state in which the sheet surface 11a of the light sheet 11 is perpendicular to the outer side surface 40a is described in detail with reference to FIGS. 4A and 4B.

In Embodiment 1, the optical axis of the irradiation optical system 30 is parallel to the X-axis, and the outer side surface 40a of the flow cell 40 is parallel to the YZ plane. Thus, as shown in FIG. 4A, a central axis 90 of light incident on the outer side surface 40a is perpendicular to the outer side surface 40a, and the sheet surface 11a of the light sheet 11 is perpendicular to the outer side surface 40a. In this case, as described above with reference to FIG. 3A, the thickness of the light sheet 11 in the second direction D2 is less likely to be affected by the outer side surface 40a, thereby enabling the imaging device 60 to take a high-definition image.

However, the central axis 90 of the light incident on the outer side surface 40a is not necessarily perpendicular to the outer side surface 40a. Specifically, the central axis 90 shown in FIG. 4A may be inclined in the first direction D1. Thus, as shown in FIG. 4B, the central axis 90 of the light incident on the outer side surface 40a is not perpendicular to the outer side surface 40a, but the sheet surface 11a of the light sheet 11 is perpendicular to the outer side surface 40a. Also in this case, as described above with reference to FIG. 3C, the thickness of the light sheet 11 in the second direction D2 is less likely to be affected by the outer side surface 40a, thereby enabling the imaging device 60 to take a high-definition image.

Referring back to FIG. 1, the condensing optical system 50 condenses the fluorescence generated from the cell 12, at the Y-axis positive side of the flow cell 40. The condensing optical system 50 may condense the fluorescence generated from the cell 12, at the Y-axis negative side of the flow cell 40. The object lens 51 condenses the fluorescence generated from the cell 12. The optical filter 52 blocks unnecessary light such as side scattered light generated from the cell 12, and causes only the fluorescence to be imaged to pass therethrough. If such unnecessary light is not concerned, the optical filter 52 may be omitted. The condenser lens 53 condenses the fluorescence transmitted through the optical filter 52. Depending on the specification of the object lens 51, the condenser lens 53 may be omitted.

The condenser lenses 54 and 56 form a Fourier plane in the condensing optical system 50. A Fourier plane may be formed by further disposing an even number of lenses between the condenser lens 56 and the phase modulation element 55.

The phase modulation element 55 is disposed on the Fourier plane in the condensing optical system 50, and modulates the phase of light to realize an extended depth of focus (EDoF). The phase modulation element 55 forms a point spread function (PSF) for obtaining the extended depth of focus. That is, the phase modulation element 55 has an effect of modulating the PSF to realize the extended depth of focus. The phase modulation element 55 is a phase modulation element that forms a spiral point spread function.

The phase modulation element 55 forms a PSF that allows light generated from a single point to be imaged onto a single focal point. Such a PSF is called SH-PSF (Single-Helix Point Spread Function). The spiral point spread function formed by the phase modulation element 55 is a single-helix point spread function. The configuration of the phase modulation element 55 will be described later with reference to FIGS. 5A and 5B.

The imaging device 60 receives, at an imaging surface 61, the fluorescence condensed by the condensing optical system 50. The imaging device 60 takes a two-dimensional image of the fluorescence, and outputs the taken two-dimensional image. The taken two-dimensional image is a cross-sectional image of the cell 12. The imaging device 60 is implemented by, for example, a color CCD. In Embodiment 1, since fluorescence having a predetermined wavelength is generated from the nucleus 12a, the imaging device 60 is configured to be able to identify at least light having this wavelength. In a case where the cell is stained by a plurality of kinds of fluorescent dyes, the imaging device 60 is configured to be able to identify lights having different wavelengths. If satisfactory sensitivity cannot be obtained by a color CCD, adjustment may be performed, such as sufficiently reducing the speed of the sample that flows in the flow cell 40.

The fluorescences having the respective wavelength bands may be separated for each wavelength band in the condensing optical system 50, and each of the separated fluorescences may be received by an imaging device or a color CCD capable of identifying only light of one wavelength band. In this case, images obtained by a plurality of imaging devices at the same timing are superposed on one another, thereby generating a single cross-sectional image. In a case where only fluorescence of one wavelength band is generated from the cell 12, the imaging device 60 may be configured to be able to identify only light of one wavelength band.

The optical axis of the condensing optical system 50 is perpendicular to the Z-axis direction which is the sample flow direction. In other words, the optical axis of the object lens 51 is perpendicular to the Z-axis. Thus, the imaging device 60 receives a portion, of the fluorescence generated from the cell 12, which goes out of the flow cell 40 without being substantially deflected by the flow cell 40, whereby the beam shape of the fluorescence applied to the imaging surface 61 is less likely to be deformed. Accordingly, a high-definition image can be taken by the imaging device 60.

The optical axis of the condensing optical system 50 may slightly deviate from the perpendicular state to the sample flow direction. As long as the optical axis of the condensing optical system 50 is substantially perpendicular to the sample flow direction, the beam shape of the fluorescence applied to the imaging surface 61 is inhibited from being deformed, whereby a high-definition image can be taken by the imaging device 60.

The optical axis of the irradiation optical system 30 and the optical axis of the condensing optical system 50 are perpendicular to each other. Thus, the imaging device 60 can image the fluorescence generated from the cross section of the cell 12, from the front side. That is, the imaging device 60 images the fluorescence not at a position that deviates in the X-axis direction with respect to the cross section of the cell 12 but in the YZ plane including the cross section of the cell 12. Thus, a process of correcting the taken image in the X-axis direction need not be performed.

The optical axis of the irradiation optical system 30 and the optical axis of the condensing optical system 50 may slightly deviate from the state of being perpendicular to each other. As long as the optical axis of the irradiation optical system 30 and the optical axis of the condensing optical system 50 are substantially perpendicular to each other, the imaging device 60 can image, from substantially the front side, the fluorescence generated from the cross section of the cell 12, which substantially eliminates the need for performing the process of correcting the taken image in the X-axis direction.

The rotation controller 70 is connected to the rotation mechanism section 32, and controls rotation of the rotation mechanism section 32. Control by the rotation controller 70 will be described later with reference to FIGS. 14A and 14B.

The information processing unit 10b includes a processing section 81, a storage section 82, a display section 83, an input section 84, and an interface 85. The processing section 81 is implemented by, for example, a CPU. The storage section 82 is implemented by, for example, a ROM, a RAM, or a hard disk. The processing section 81 controls the respective components in the information processing unit 10b via the interface 85, and controls the imaging device 60 and the rotation controller 70.

The processing section 81 generates a three-dimensional image on the basis of the images obtained by the imaging device 60. Specifically, the imaging device 60 generates a three-dimensional image by superposing a plurality of cross-sectional images obtained from one cell. The display section 83 is a display for displaying, for example, the processing result of the processing section 81. The input section 84 is a keyboard and a mouse for receiving an input of instruction by an operator.

Next, the configuration of the phase modulation element 55 is described.

Figure 5A:
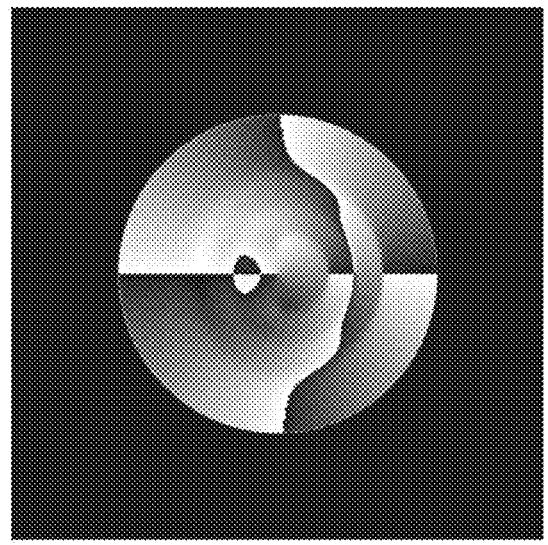
FIG. 5A is a diagram showing a phase modulation pattern of a spatial light modulator according to Embodiment 1.

The phase modulation element 55 performs phase modulation on fluorescence that transmits therethrough. As for the phase modulation element 55, a transmission type spatial light modulator using a liquid crystal panel can be used, for example. The spatial light modulator is capable of performing phase modulation at 256 gray levels for each pixel. A phase modulation pattern for forming a single-helix PSF is set as shown in FIG. 5A, for example. The phase modulation pattern is a pattern distribution of gray levels set for all pixels.

In FIG. 5A, pixels having the gray level of 0 are shown in black, and pixels having the gray level of 255 are shown in white. Each pixel having the gray level of 0 does not modulate the phase of the incident fluorescence. The phase of the fluorescence incident on each pixel having the gray level of 255 is shifted by $2\pi$ with respect to the phase of the fluorescence incident on the pixel having the gray level of 0.

Figure 5B:
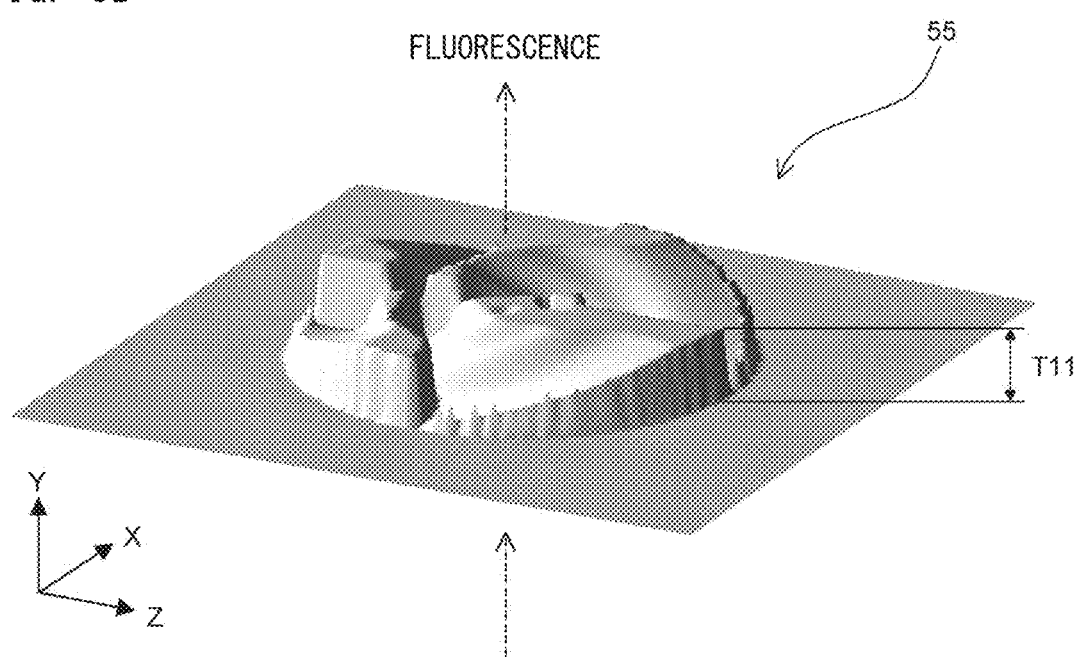
FIG. 5B is a diagram schematically showing the structure of a phase plate according to Embodiment 1.

As shown in FIG. 5B, a phase plate can also be used as the phase modulation element 55. The phase plate is formed of a transparent material such as acrylic resin. The material forming the phase plate is not necessarily transparent. Any material can be used as long as it can transmit light. When the thickness T11 of the phase plate varies, the phase of the fluorescence transmitting therethrough varies. The thickness T11 of each portion of the phase plate is adjusted such that phase modulation similar to the phase modulation pattern shown in FIG. 5A is generated.

Figure 6:
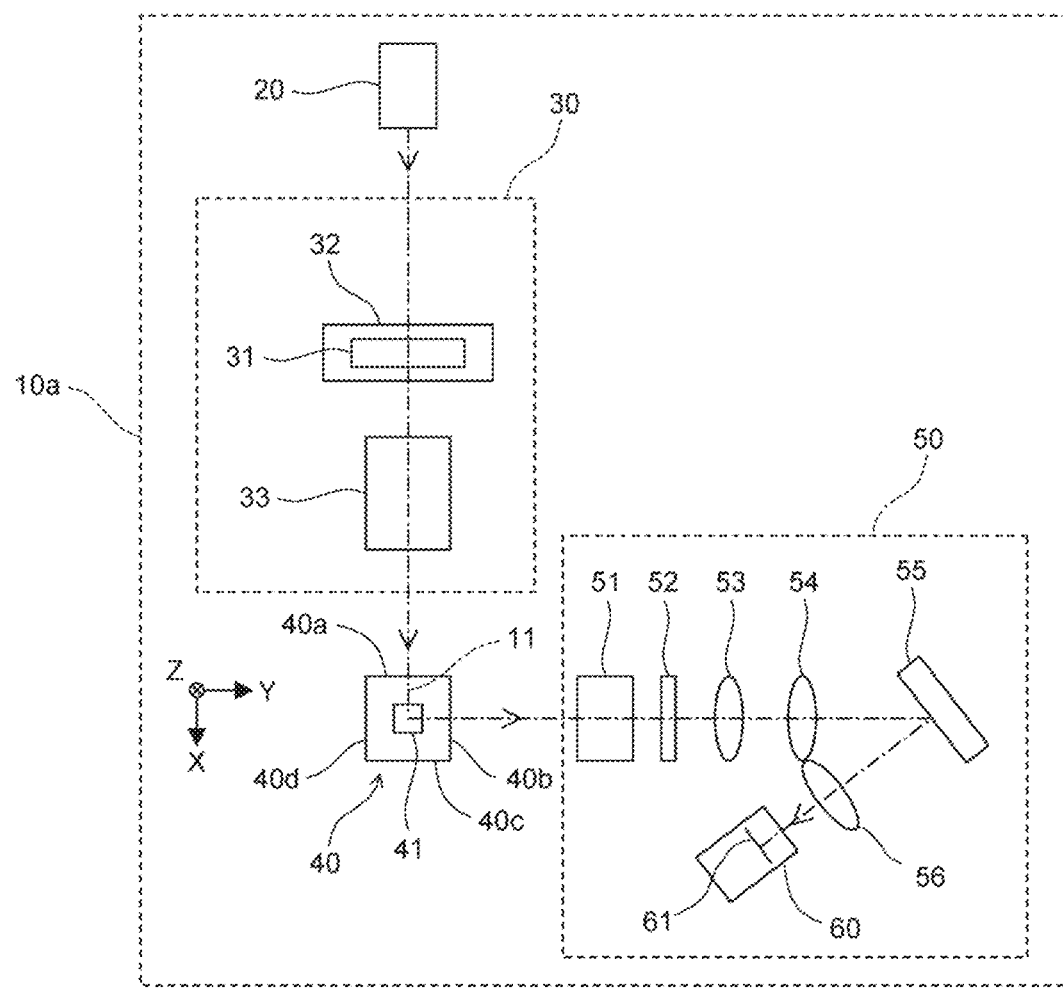
FIG. 6 is a diagram showing the structure of an imaging unit in a case where a deformable mirror is used as a phase modulation element, according to Embodiment 1.

A deformable mirror can also be used as the phase modulation element 55. When a deformable mirror is used as the phase modulation element 55, the configuration of the imaging unit 10a is changed as shown in FIG. 6. Also in this case, the phase modulation element 55 is disposed on the Fourier plane of the condensing optical system 50. The fluorescence condensed by the object lens 51 is reflected by the phase modulation element 55, thereby being subjected to phase modulation. Thus, a single-helix PSF is formed at the imaging surface 61 of the imaging device 60. In the configuration of FIG. 6, a reflection type spatial light modulator may be used as the phase modulation element 55. In this case, for example, a polarizer is disposed between the object lens 51 and the optical filter 52.

As described above, the depth of focus of the condensing optical system 50 can be extended by providing the phase modulation element 55 in the condensing optical system 50.

Figure 7A:
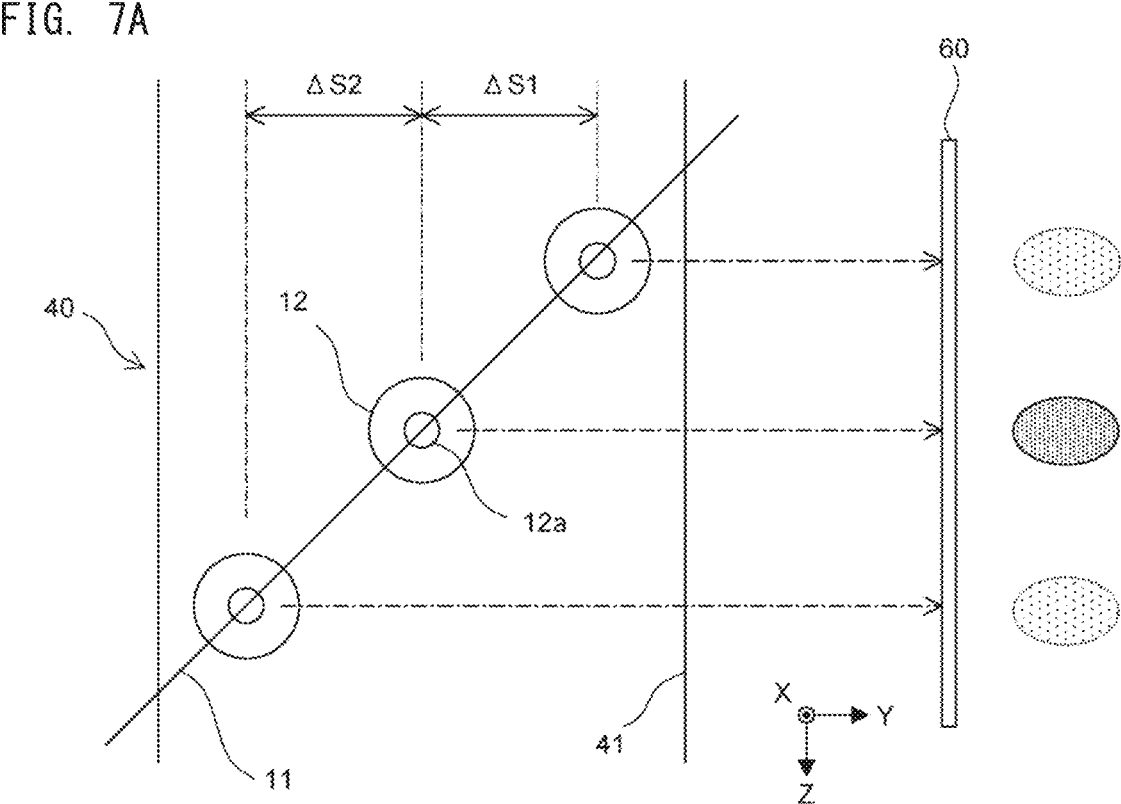
FIG. 7A is a diagram showing an imaging state of an image in an imaging device in a case where a phase modulation element is not provided in a condensing optical system.

FIG. 7A schematically shows an imaging state in a case where the phase modulation element 55 is not provided in the condensing optical system 50. In FIG. 7A, three cells 12 flow in the flow path 41 of the flow cell 40. The flow path 41 of the flow cell 40 has a width enough to allow a plurality of cells to simultaneously flow at positions in the width direction. The light sheet 11 has a width that covers at least the entirety of the flow path 41. The imaging device 60 has a width enough to receive at least light from the region of the light sheet 11 included in the flow path 41. The three cells 12 simultaneously cross the light sheet 11. The cross sections, of the nuclei 12a of the three cells 12, cut by the light sheet 11 are simultaneously imaged by the imaging device 60.

The positions at which the three cells 12 flow are shifted from each other in the Y-axis direction. The upper and lower cells 12 are shifted by distances AS1 and AS2, respectively, with respect to the center cell 12 in the Y-axis direction. In a case where the focus position of the condensing optical system 50 is set at the center of the flow path 41 in the Y-axis direction, the cross-sectional image of the nucleus 12a of the center cell 12 is satisfactorily taken. However, regarding the upper and lower cells 12, since these cells are shifted from the focus position of the condensing optical system 50, the cross-sectional images of the nuclei 12a thereof cannot be satisfactorily taken. On the right side in FIG. 7A, the cross-sectional images of the nuclei 12a of the three cells 12 are schematically shown.

Figure 7B:
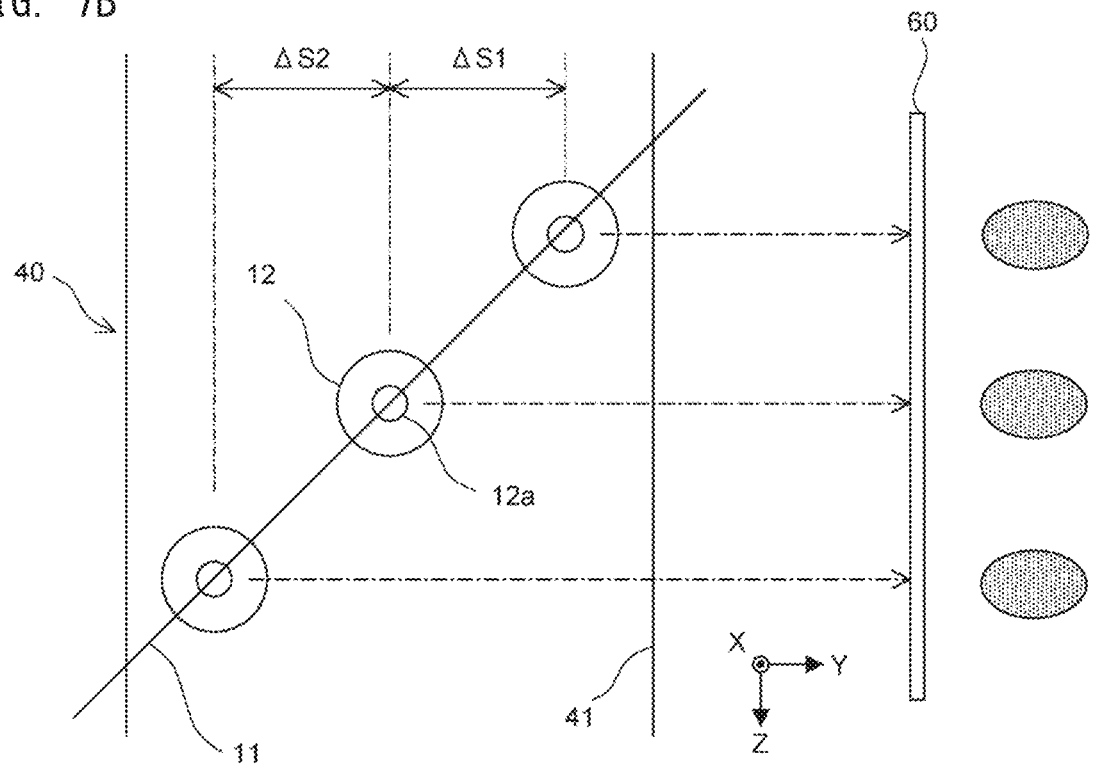
FIG. 7B is a diagram showing an imaging state of an image in the imaging device according to Embodiment 1.

On the other hand, in the case where the phase modulation element 55 that forms the spiral PSF is provided in the condensing optical system 50, the depth of focus of the condensing optical system 50 is extended. Therefore, as shown in FIG. 7B, even when the positions of the upper and lower cells 12 are shifted from the center of the flow path 41 in the Y-axis direction, that is, in the optical axis direction of the condensing optical system 50, it is possible to satisfactorily obtain the cross-sectional images of the nuclei 12a of these cells 12. Thus, regarding the plurality of cells 12 simultaneously crossing the light sheet 11, high-quality cross-sectional images of the nuclei 12a thereof can be obtained.

Also in one cell 12, regarding the distance between the cross section of the nucleus 12a cut by the light sheet 11 and the imaging surface of the imaging device 60, the distance on the Z-axis positive side of the cross section is short and the distance on the Z-axis negative side of the cross section is long. Therefore, when the phase modulation element 55 is not provided in the condensing optical system 50, partial focus deviation may occur also within the cross-sectional image of one nucleus 12a. In contrast, when the phase modulation element 55 is provided in the condensing optical system 50, since the depth of focus of the condensing optical system 50 is extended as described above, partial focus deviation does not occur within the cross-sectional image of one nucleus 12a. Therefore, an excellent cross-sectional image of the nucleus 12a can be obtained.

However, when the phase modulation element 55 is provided in the condensing optical system 50, distortion occurs in the cross-sectional image of the nucleus 12a due to the phase modulation effect of the phase modulation element 55.

Figure 8:
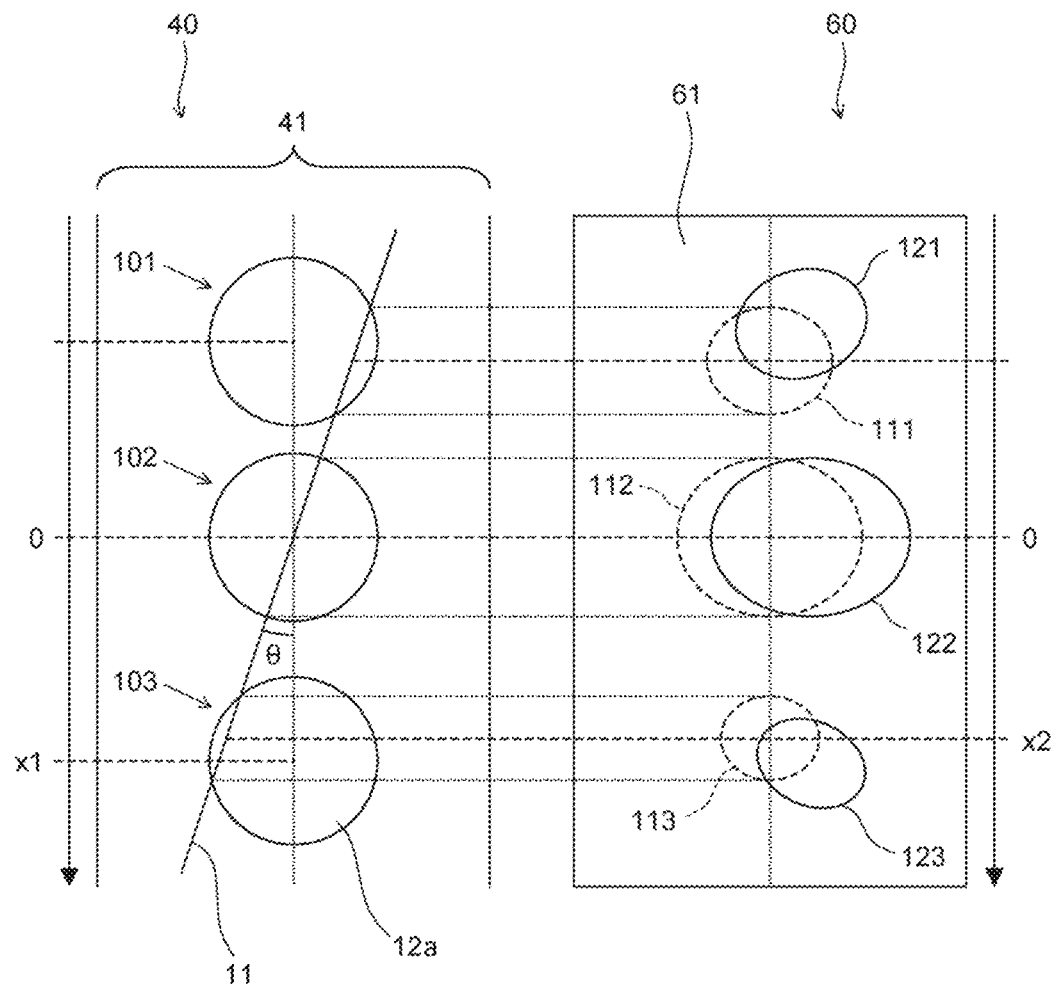
FIG. 8 is a diagram schematically showing distortion of an image caused by an effect of the phase modulation element, according to Embodiment 1.

FIG. 8 schematically shows this distortion. With reference to FIG. 8, for convenience, distortion of the cross-sectional image of one nucleus 12a is described for a case where the one nucleus 12a crosses the light sheet 11 while flowing along the flow path 41. In this case, with movement of the nucleus 12a, the position of the cross section of the nucleus 12a cut by the light sheet 11 changes in the Y-axis direction. That is, the position of the cross section of the nucleus 12a is more displaced in the Y-axis negative direction when the nucleus 12a is located at a position 102 than when the nucleus 12a is located at a position 101. Further, the position of the cross section of the nucleus 12a is more displaced in the Y-axis negative direction when the nucleus 12a is located at a position 103 than when the nucleus 12a is located at the position 102. Strictly speaking, regarding the cross section of the nucleus 12a cut by the light sheet 11, the distance between each portion in the cross section and the imaging surface of the imaging device 60 changes depending on the position of the cross section in the Z-axis direction.

When the phase modulation element 55 is not provided in the condensing optical system 50, fluorescences generated from these cross sections are applied to irradiation areas 111, 112, and 113 indicated by broken lines, respectively, on the imaging surface 61 of the imaging device 60. However, when the phase modulation element 55 is provided in the condensing optical system 50, the fluorescences generated from the respective cross sections are applied to irradiation areas 121, 122, and 123 indicated by solid lines, respectively, due to the phase modulating effect of the phase modulation element 55. The irradiation areas 121, 122, and 123 are displaced and deformed in the direction of the arrow shown in FIG. 8 with respect to the irradiation areas 111, 112, and 113. This distortion is caused by that each portion in the cross section of the nucleus 12a is shifted in the direction according to the distance between the portion and the imaging surface 61, due to the effect of the single-helix PSF. That is, this distortion is based on the effect of the single-helix PSF formed by the phase modulation element 55.

Figure 9:
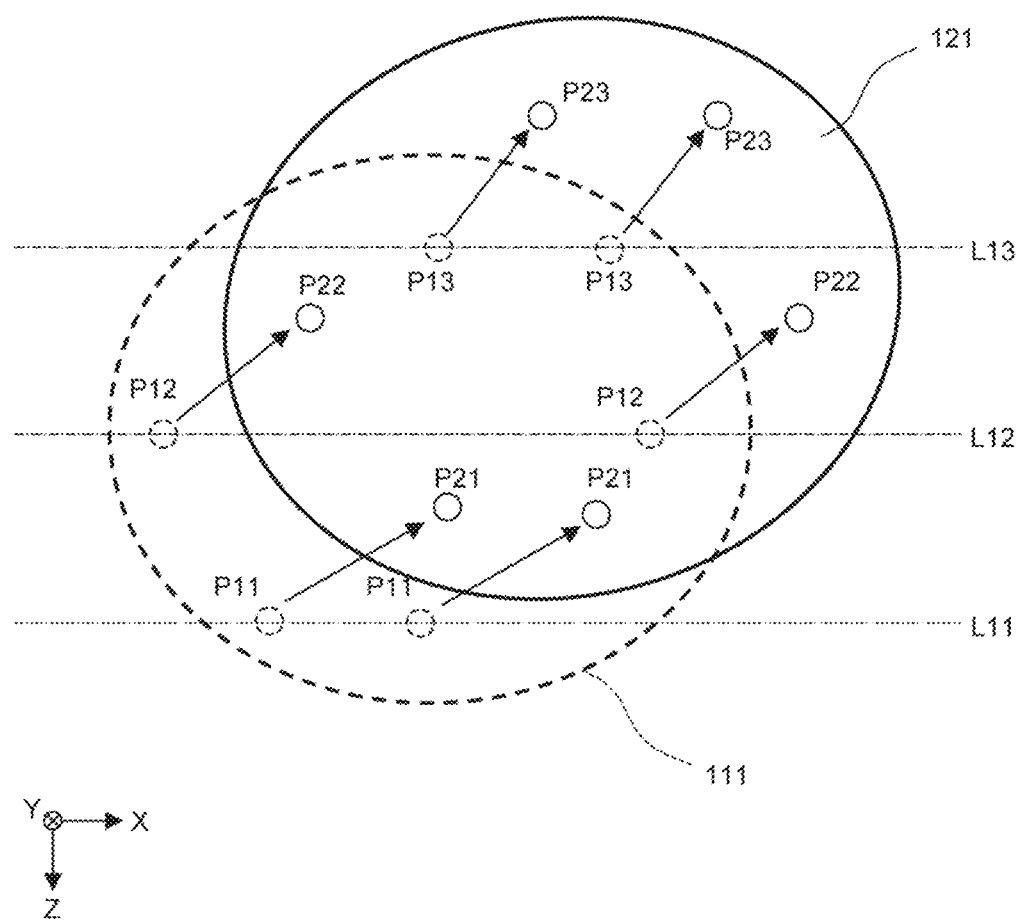
FIG. 9 is a diagram schematically showing shifting of irradiation positions caused by the effect of the phase modulation element, according to Embodiment 1.

As shown in FIG. 9, when the phase modulation element 55 is not provided in the condensing optical system 50, fluorescences generated from portions of the cross section of the nucleus 12a are applied to, for example, positions P11, P12, and P13 in the irradiation area 111. On the other hand, when the phase modulation element 55 is provided in the condensing optical system 50, fluorescences generated from the portions of the cross section of the nucleus 12a are applied to positions P21, P22, and P23 in the irradiation area 121. Thus, when the phase modulation element 55 is provided in the condensing optical system 50, the irradiation positions of the fluorescences generated from the respective portions of the cross section of the nucleus 12a are shifted with respect to those in the case where the phase modulation element 55 is not provided in the condensing optical system 50.

Figure 10A:
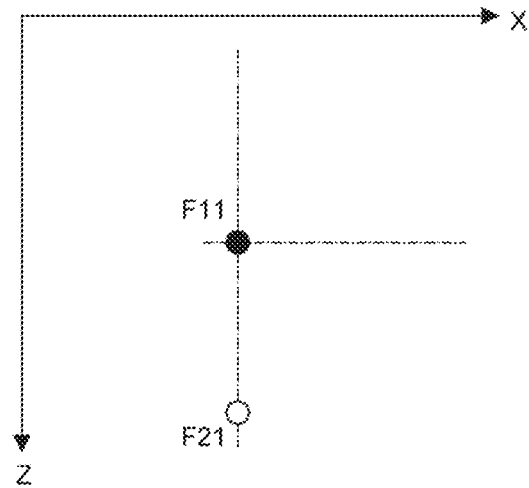
FIG. 10A is a diagram showing the effect of the phase modulation element according to Embodiment 1.
Figure 10B:
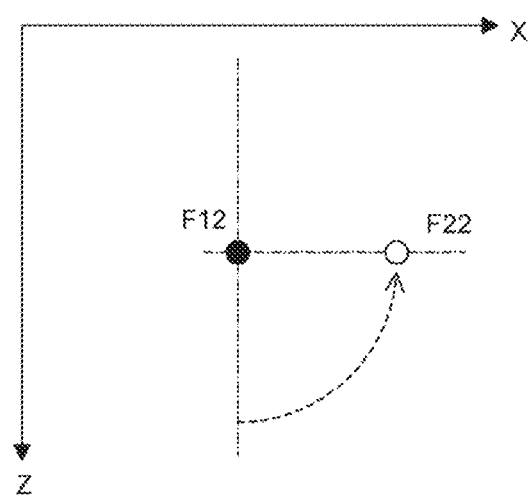
FIG. 10B is a diagram showing the effect of the phase modulation element according to Embodiment 1.
Figure 10C:
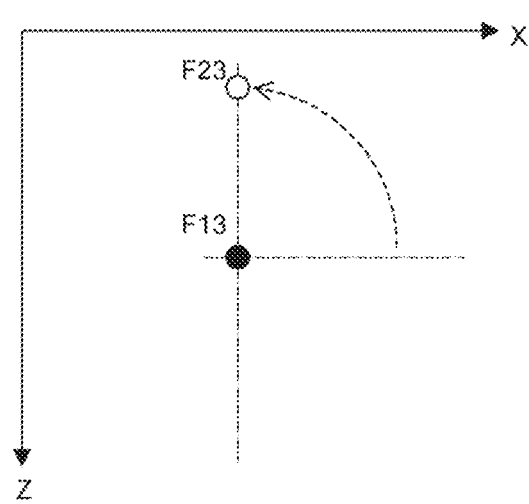
FIG. 10C is a diagram showing the effect of the phase modulation element according to Embodiment 1.

As shown in FIGS. 10A to 10C, when the phase modulation element 55 forms the single-helix PSF, the positional relationship between the fluorescence irradiation positions F11, F12, and F13 on the imaging surface 61 in the case where the phase modulation element 55 is not provided and the fluorescence irradiation positions F21, F22, and F23 on the imaging surface 61 in the case where the phase modulation element 55 is provided, changes depending on the distance between the imaging surface 61 and the bright point of the fluorescence.

As shown in FIG. 10A, when the bright point of the fluorescence is at a position farthest from the imaging surface 61, that is, when the fluorescence is generated at a position most negative side, in the Y-axis direction, of the light sheet 11 included in the flow path 41, the fluorescence irradiation position F21 on the imaging surface 61 is displaced by a predetermined distance in the Z-axis positive direction with respect to the irradiation position F11 in the case where the phase modulation element 55 is not provided.

As shown in FIG. 10C, when the bright point of the fluorescence is at a position closest to the imaging surface 61, that is, when the fluorescence is generated at a position most positive side, in the Y-axis direction, of the light sheet 11 included in the flow path 41, the fluorescence irradiation position F23 on the imaging surface 61 is displaced by a predetermined distance in the Z-axis negative direction with respect to the irradiation position F13 in the case where the phase modulation element 55 is not provided.

As shown in FIG. 10B, when the bright point of the fluorescence is at an intermediate position between the bright point position shown in FIG. 10A and the bright point position shown in FIG. 10C in the Y-axis direction, that is, when the fluorescence is generated from an intermediate position, in the Y-axis direction, of the light sheet 11 included in the flow path 41, the fluorescence irradiation position F22 on the imaging surface 61 is displaced by a predetermined distance in the X-axis positive direction with respect to the irradiation position F12 in the case where the phase modulation element 55 is not provided.

When the fluorescence irradiation positions F11, F12, and F13 in the case where the phase modulation element 55 is provided are connected to the fluorescence irradiation positions F21, F22, and F23 in the case where the phase modulation element 55 is not provided, respectively, by straight lines, each straight line rotates in parallel to the X-Z plane in accordance with the distance between the imaging surface 61 and the bright point of the fluorescence.

The above-described optical effect causes shifting of the irradiation positions shown in FIG. 9. In FIG. 9, when lines L11, L12, and L13 parallel to the X-axis direction are set on the imaging surface 61, the distances in the Y-axis direction between the light sheet 11 and all the positions on the line L11 are constant, the distances in the Y-axis direction between the light sheet 11 and all the positions on the line L12 are constant, and the distance in the Y-axis direction between the light sheet 11 and all the positions on the line L13 are constant.

Therefore, all the fluorescences applied to the line L11 in the case where the phase modulation element 55 is not provided are shifted by the same distance in the same direction, due to the effect of the phase modulation element 55. All the fluorescences applied to the line L12 in the case where the phase modulation element 55 is not provided are shifted by the same distance in the same direction, due to the effect of the phase modulation element 55. All the fluorescences applied to the line L13 in the case where the phase modulation element 55 is not provided are shifted by the same distance in the same direction, due to the effect of the phase modulation element 55.

Therefore, the fluorescences applied to the positions P11, P12, and P13 in the irradiation area 111 in the case where the phase modulation element 55 is not provided, are applied to the positions P21, P22, and P23 in the irradiation area 121 in the case where the phase modulation element 55 is provided, respectively. A shift vector from the position P11 to the position P21, a shift vector from the position P12 to the position P22, and a shift vector from the position P13 to the position P23 are different from each other because the distances between the light sheet 11 and the lines L11, L12, and L13 in the Y-axis direction are different from each other, on the basis of the optical effect described with reference to FIGS. 10A to 10C. Therefore, the irradiation area 121 in the case where the phase modulation element 55 is provided is shifted while being deformed with respect to the irradiation area 111 in the case where the phase modulation element 55 is not provided. Thus, distortion occurs in the irradiation area 121.

The irradiation areas 122 and 123 shown in FIG. 8 are also shifted while being deformed with respect to the irradiation area 111 due to the optical effect of the phase modulation element 55, whereby distortion occurs in each of the irradiation areas 122 and 123. Since the positions, in the Y-axis direction, of the cross sections of the nucleus 12a corresponding to the irradiation areas 121, 122, and 123 are different from each other, distortions of the irradiation areas 121, 122, and 123 are different from each other. Therefore, if the images of the irradiation areas 121, 122, and 123 are used for generation of a three-dimensional image of the nucleus 12a without being corrected, the quality of the three-dimensional image may be degraded.

In Embodiment 1, the cross-sectional images of the nucleus 12a are subjected to correction for eliminating distortions, and a three-dimensional image of the nucleus 12a is generated by using the corrected cross-sectional images. Thus, the quality of the three-dimensional image can be improved. The distortion correction is performed by the processing section 81 shown in FIG. 1.

In this correction, the processing section 81 causes image elements forming the cross-sectional image to shift to positions at which displacement based on the PSF is corrected, respectively. For example, the processing section 81 performs a process of shifting an image element that is obtained by the imaging device 60 at each irradiation position in the irradiation area 121 shown in FIG. 9, to a position corresponding to each irradiation position in the irradiation area 111. Specifically, the processing section 81 performing a process of shifting the image elements obtained from the positions P21, P22, and P23 to the positions corresponding to the positions P11, P12, and P13. The processing section 81 performs processes similar to the above process, on the image elements obtained from all the irradiation positions in the irradiation area 121. Thus, distortion of the entire taken image can be appropriately corrected by performing the process of individually shifting the image elements.

In Embodiment 1, each image element is regarded as an image portion obtained for each pixel in the imaging device 60. Thus, when each image element to be corrected is set to an image element obtained from each pixel that is the minimum unit of imaging of the imaging device 60, distortion of the taken image can be corrected with high accuracy.

The image element regarded as a unit of distortion correction is not necessarily set for each pixel of the imaging device 60. An image portion obtained from a plurality of pixels included in a predetermined block unit may be regarded as an image element corresponding to a unit of distortion correction.

A specific process for distortion correction is as follows.

Figures 11A, 11B:
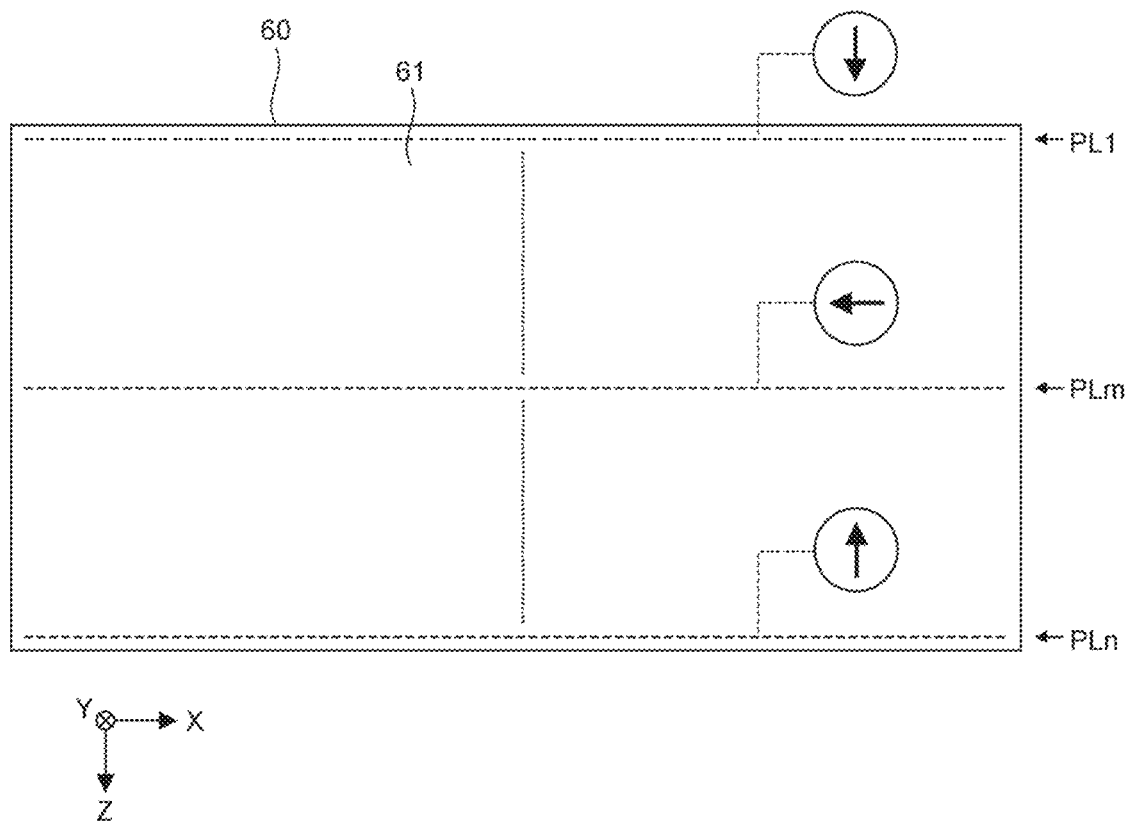
FIG. 11A is a diagram explaining a process of correcting image elements in each of pixel lines of the imaging device, according to Embodiment 1.
FIG. 11B is a table showing the contents of correction vectors according to Embodiment 1.

As shown in FIG. 11A, on the imaging surface 61 of the imaging device 60, lines of pixels arranged in the X-axis direction are present. There are n lines of pixels from the uppermost pixel line PL1 to the lowermost pixel line PLn. As shown in FIG. 8, the light sheet 11 is inclined, from the state parallel to the imaging surface 61, by a predetermined angle in the direction parallel to the Y-Z plane. Therefore, the distances, in the Y-axis direction, between the light sheet 11 and the respective pixels on the pixel line PL1 are constant. Also regarding other pixel lines, the distances, in the Y-axis direction, between the light sheet 11 and the respective pixels on one pixel line are constant. The distance, in the Y-axis direction, between the light sheet 11 and each pixel line differs per pixel line.

Therefore, fluorescences generated from the positions, on the light sheet 11, by the same distance apart from the imaging surface 61 in the Y-axis direction are incident on the respective pixels on the same pixel line. For example, in FIG. 9, the fluorescences respectively incident on the two positions P21 are incident on pixels on the same pixel line, the fluorescences respectively incident on the two positions P22 are incident on pixels on the same pixel line, and the fluorescences respectively incident on the two positions P23 are incident on pixels on the same pixel line.

The processing section 81 assigns, to each pixel line, as a correction vector, a vector that is opposite to each vector indicated by an arrow in FIG. 9. Then, the processing section 81 causes image elements obtained from the respective pixels on one pixel line to be shifted by the correction vector that is set for this pixel line. The processing section 81 executes this process on all the pixel lines. Thereby, the respective image elements in the cross-sectional image are shifted to the positions in the case where the phase modulation element 55 is not provided. Thus, distortion of the cross-sectional image is corrected.

In this correction, the processing section 81 executes, for example, a process of mapping, in a memory, pixel values obtained from all the pixels on the imaging surface 61, and shifting the mapped pixel values on the memory in accordance with the correction vectors. Alternatively, in this correction, the processing section 81 executes a process of causing registers to hold the pixel values obtained from the pixels on the respective pixel lines such that each register corresponds to one pixel line, and developing, on a memory, the pixel values held in the respective registers on the basis of the correction vectors assigned to the respective pixel lines.

In FIG. 11A, the correction vectors assigned to the respective pixel lines are schematically shown as arrows. Specifically, the correction vectors for the respective pixel lines are represented on a table as shown in FIG. 11B. An X correction value is a correction value in the X-axis direction, and is positive in the X-axis positive direction. A Z correction value is a correction value in the Z-axis direction, and is positive in the Z-axis positive direction. The processing section 81 causes the image elements, i.e., the pixel values, obtained from the respective pixels on the respective pixel lines to be shifted by the correction vectors thus defined.

As described above, the processing section 81 causes the respective image elements obtained from each pixel line that receives the fluorescence generated from the same position in the optical axis direction of the condensing optical system 50, to be shifted in accordance with the direction and distance based on the bright point of the fluorescence, that is, in accordance with the correction vector, thereby eliminating distortion of the cross-sectional image of the nucleus 12a. Thus, distortion of the cross-sectional image can be easily and appropriately eliminated.

In Embodiment 1, as shown in FIGS. 10A to 10C, the direction of displacement of each irradiation position on the imaging surface 61 is set within the range of 180° from the Z-axis positive direction to the Z-axis negative direction. However, the range of the direction of displacement of the irradiation position is not limited thereto. However, if the range of the direction of displacement of the irradiation position exceeds 180°, fluorescences generated from the positions, on the light sheet 11, having different distances from the imaging surface 61 may be simultaneously incident on some pixel lines. In this case, accuracy of distortion correction for the cross-sectional image is degraded. Therefore, the PSF of the phase modulation element 55 is preferably set such that the direction of displacement of the irradiation position on the imaging surface 61 is within the range of 180° from the Z-axis positive direction to the Z-axis negative direction.

Next, description is given of aspect-ratio correction and position adjustment when cross-sectional images having been subjected to distortion correction are superposed.

As shown in FIG. 8, the nucleus 12a in the cell 12 flows in the flow path 41 of the flow cell 40 in the Z-axis positive direction. At this time, when the nucleus 12a passes through the light sheet 11, fluorescence occurs from the cross section of the nucleus 12a to which the light sheet 11 is applied, and the generated fluorescence is applied to the imaging surface 61 of the imaging device 60. In FIG. 8, the nucleus 12a is shown as a sphere, for convenience. Assuming that the nucleus 12a is located at the positions 101 to 103 in the flow path 41 in order, fluorescences generated from the nucleus 12a located at the positions 101 to 103 are applied to the irradiation areas 121 to 123 on the imaging surface 61, respectively. These irradiation areas 121 to 123 are substantially corrected, through the aforementioned distortion correction, to the irradiation areas 111 to 113 in the case where the phase modulation element 55 is not provided.

Since the light sheet 11 is inclined with respect to the Z-axis direction, the length, in the Z-axis direction, of each irradiation area on the imaging surface 61 is shorter than the length, in the first direction D1, of the corresponding cross section to which the light sheet 11 is applied. Specifically, the length, in the Z-axis direction, of the irradiation area on the imaging surface 61 has a value obtained by multiplying the length, in the first direction D1, of the corresponding cross section to which the light sheet 11 is applied, by cos θ. Therefore, by multiplying the length of the irradiation area in the Z-axis direction by 1/cos θ, the distortion-corrected irradiation area can be corrected to have an appropriate aspect ratio in which the actual cross-sectional shape is reflected.

It is assumed that, when the nucleus 12a is at the position 102, the light sheet 11 is applied to the center of the nucleus 12a. At this time, assuming that the position of the nucleus 12a on the Z-axis is 0, the position of the irradiation area 112 on the Z-axis is also 0. However, when the nucleus 12a is at a position different from the position 102, the light sheet 11 is not applied to the center of the nucleus 12a. In this case, displacement occurs between the position of the nucleus 12a and the position of the distortion-corrected irradiation area.

It is assumed that the position, on the Z-axis, of the nucleus 12a at the position 103 is x1, and the position, on the Z-axis, of the irradiation area 113 is x2. That is, it is assumed that the amount of movement of the nucleus 12a in the flow path 41 of the flow cell 40 is x1, and the amount of movement of the image of the nucleus 12a on the imaging surface 61 is x2. When the angle of inclination of the light sheet 11 with respect to the sample flow direction is θ, x2 is calculated according to the following formula (1).

$$x2 = x1(1 - \sin^2 \theta) \quad (1)$$

Figure 12A:
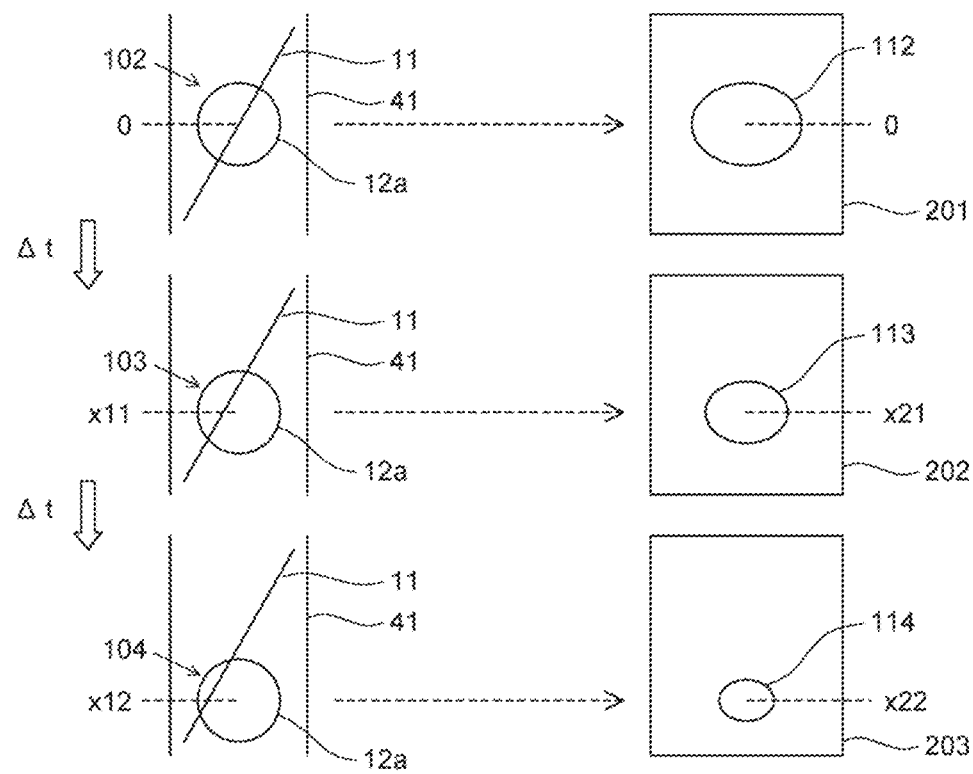
FIG. 12A is a diagram explaining aspect-ratio correction and position adjustment when images obtained by the imaging device according to Embodiment 1 are superposed on one another.

It is assumed that, as shown in FIG. 12A, distortion-corrected images 201 to 203 are obtained on the basis of the nucleus 12a at the positions 102 to 103, respectively. In the images 201 to 203, the distortion-corrected irradiation areas 112 to 114 corresponding to the nucleus 12a are included.

In order to superpose the images 201 to 203, for example, a timing at which the image 201 in which the position of the irradiation area on the Z-axis is 0, is set as a reference time. The amount of movement x11 of the nucleus 12a when an imaging interval Δt has passed from the reference time can be calculated by multiplying Δt by the sample flow speed. At this time, the position x21 of the irradiation area 113 can be obtained by substituting x11 for x1 in the above formula (1). Likewise, the amount of movement x12 of the nucleus 12a when an imaging interval 2Δt has passed from the reference time can be calculated by multiplying 2Δt by the sample flow speed. At this time, the position x22 of the irradiation area 114 can be obtained by substituting x12 for x1 in the above formula (1). Then, in the image 202, the irradiation area 113 is shifted by x21 in the direction approaching the position 0 on the Z-axis. Likewise, also in the image 203, the irradiation area 114 is shifted by x22 in the direction approaching the position 0 on the Z-axis.

The images taken by the imaging device 60 are successively stored in the storage section 82. The processing section 81 of the information processing unit 10b groups all the distortion-corrected images from the first cross-sectional image to the last cross-sectional image that have been obtained from one nucleus 12a, among a plurality of images stored in the storage section 82. In grouping the distortion-corrected images, a distortion-corrected image previous to the first distortion-corrected image of the nucleus 12a and a distortion-corrected image subsequent to the last distortion-corrected image of the nucleus 12a may be included in the group. The interval of imaging by the imaging device 60 is determined on the basis of the speed of the sample that flows in the flow path 41, the size of the cell, the thickness of the light sheet 11 in the second direction D2, etc., such that the number of images taken from one cell is about 2 to 100.

Figure 12B:
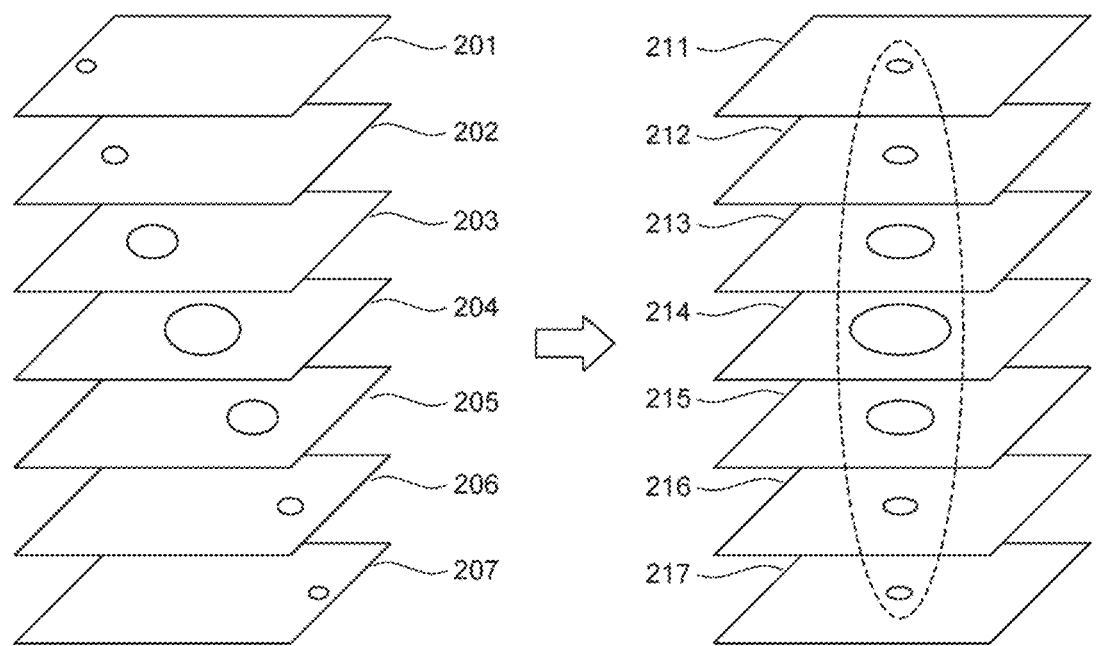
FIG. 12B is a diagram explaining aspect-ratio correction and position adjustment when images obtained by the imaging device according to Embodiment 1 are superposed on one another.

For example, as shown on the left side in FIG. 12B, the processing section 81 groups the distortion-corrected images 201 to 207. The processing section 81 subjects the grouped distortion-corrected images 201 to 207 to correction of the aspect ratios of the irradiation areas on the respective images as described above. Then, the processing section 81 subjects the aspect-ratio-corrected images 201 to 207 to position adjustment for the irradiation areas on the respective images as described above. Thus, as shown on the right side in FIG. 12B, images 211 to 217 are obtained which have been subjected to the above-described distortion correction, aspect-ratio correction, and adjustment of center positions of the irradiation areas.

Then, the processing section 81 superposes the images 211 to 217 which have been subjected to the aspect-ratio correction and the position adjustment, thereby generating an appropriate three-dimensional image of one nucleus 12a. Thus, a high-quality three-dimensional image can be obtained.

The aspect-ratio correction and the position adjustment performed for generating a three-dimensional image are not limited to the above-described methods, and the following methods may be adopted, for example.

A sample containing spherical particles such as fluorescence beads is caused to flow in the flow cell 40, and images of each particle are taken by the imaging device 60. In each of the taken images, a center coordinate of the particle cross-section in the flow direction is obtained. Then, to what extent each image should be shifted to make the center coordinates of the particle cross-sections coincide with each other, is calculated as a parameter for correction of displacement. Further, in any one of the images, to what extent the image should be extended in the flow direction to make the particle cross-section completely round, is calculated as a parameter for correction of the aspect ratio. Two parameters thus obtained are stored in the storage section 82.

When a three-dimensional image is generated on the basis of an actual sample, the processing section 81 subjects each distortion-corrected image to aspect-ratio correction and position adjustment, by using the two parameters stored in the storage section 82. Then, the processing section 81 superposes the images that have been subjected to the aspect-ratio correction and the position adjustment, thereby generating a three-dimensional image. In this case, the aspect-ratio correction and the position adjustment can be performed on the basis of the actual states of the optical system and the like in the cell imaging apparatus 10, whereby a high-definition three-dimensional image can be generated. The two parameters may be obtained based on one bead, but preferably are obtained by averaging parameters obtained based on a plurality of beads.

Next, the relationship between inclination of the light sheet 11 and imaging accuracy is described.

Figure 13A:
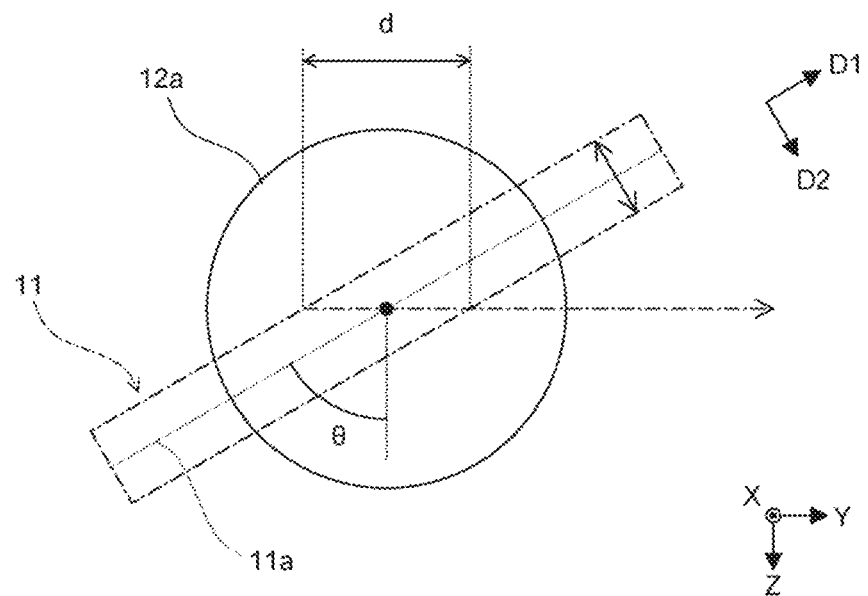
FIG. 13A is a diagram explaining the relationship between inclination of the light sheet and imaging accuracy, according to Embodiment 1.
Figure 13B:
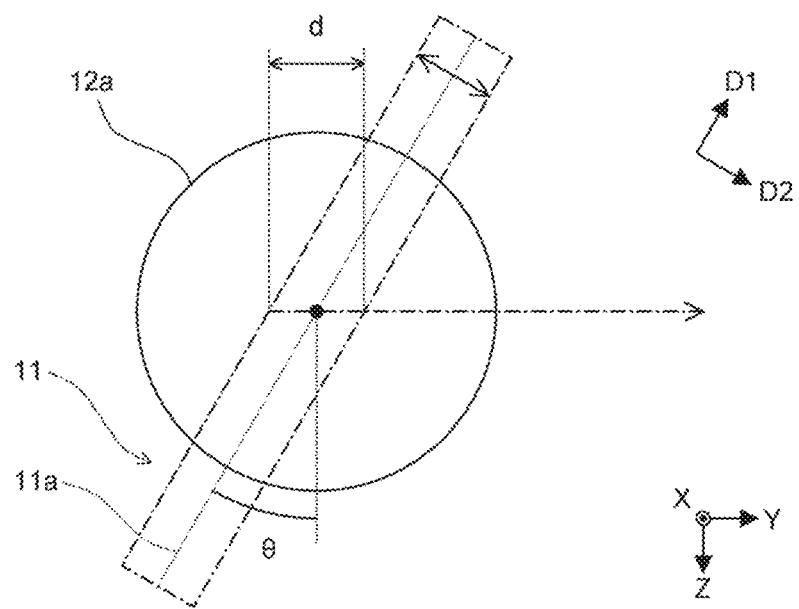
FIG. 13B is a diagram explaining the relationship between inclination of the light sheet and imaging accuracy, according to Embodiment 1.

As shown in FIGS. 13A and 13B, the light sheet 11 has a predetermined thickness in the second direction D2 according to the rotational position of the optical lens 31. When the light sheet 11 is applied to the center of the nucleus 12a, the thickness of the light sheet 11 in the optical axis direction of the condensing optical system 50, i.e., in the Y-axis direction, is equal to a width d. In this case, fluorescence is generated not only from the center of the nucleus 12a but also from a portion of the nucleus 12a included in the range of the width d. Therefore, when imaging of the center of the nucleus 12a is performed, the fluorescence generated from the portion, of the nucleus 12a, other than the center portion becomes a noise component. Such a noise component causes background noise of the taken image, and therefore is preferably as small as possible.

As shown in FIG. 13A, the width d increases as the inclination angle θ of the sheet surface 11a with respect to the Z-axis approaches 90°. On the other hand, as shown in FIG. 13B, the width d decreases as the inclination angle θ of the sheet surface 11a with respect to the Z-axis approaches 0°. Therefore, in order to reduce the noise component, the angle θ is preferably as small as possible. However, as described above, when the angle θ is 0°, a plurality of different cross-sectional images cannot be obtained. Therefore, the angle θ needs to be greater than at least 0°.

Next, description is given of the conditions for the angle θ that allows obtainment of all the cross sections while reducing the noise component.

Figure 14A:
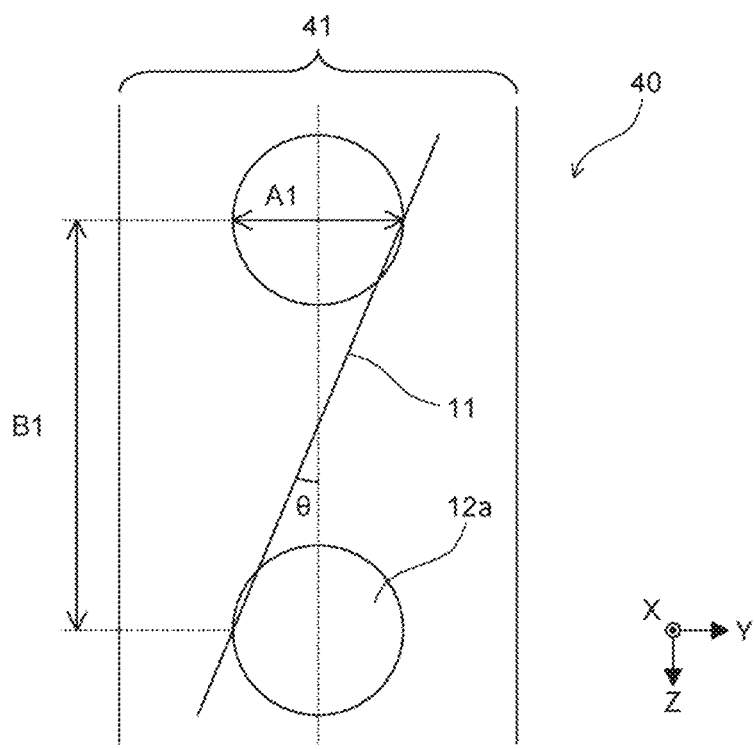
FIG. 14A is a diagram explaining the conditions for an angle that allows obtainment of all cross sections while reducing noise component, according to Embodiment 1.

As shown in FIG. 14A, it is assumed that the diameter of the nucleus 12a is A1, and the size of an imaging field-of-view in the flow path 41, i.e., the width, in the Z-axis direction, of the flow path 41 that can be imaged, is B1. In order to obtain all the cross sections of the nucleus 12a while reducing the angle θ for reduction of the noise component, the light sheet 11 needs to cover one end, of the nucleus 12a, positioned at an upper end of the imaging field-of-view and the other end, of the nucleus 12a, positioned at a lower end of the imaging field-of-view. Therefore, an optimum angle θ is calculated from the following formula (2).

$$\tan \theta = A1/B1 \quad (2)$$

When the angle θ is set so as to satisfy the formula (2), a high-definition image with reduced background noise can be taken while obtaining all the cross-sectional images of the nucleus 12a.

Next, description is given of a process of applying the optimum angle θ as described above to the cell imaging apparatus 10.

Figure 14B:
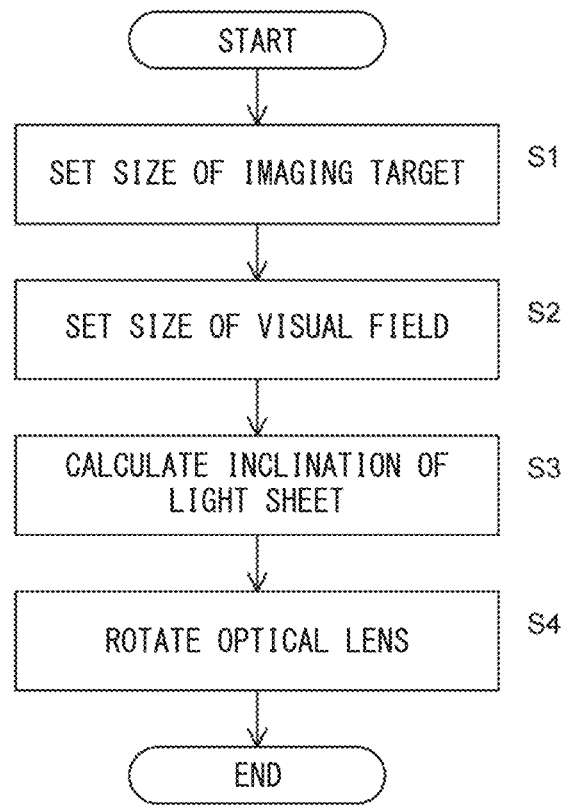
FIG. 14B is a flowchart showing process steps for applying an optimum angle to the cell imaging apparatus according to Embodiment 1.

As shown in FIG. 14B, in step S1, the processing section 81 receives a numerical value that is inputted by a user through the input section 84, and sets, on the rotation controller 70, the received numerical value as an average size of an imaging target, i.e., as an average width of the imaging target in the optical axis direction of the condensing optical system 50. In Embodiment 1, the user inputs an average diameter of the nucleus 12a.

In step S1, the processing section 81 may cause the display section 83 to display a list of imaging targets, and may receive an imaging target that is selected by the user through the input section 84. In this case, the processing section 81 reads, from a mapping table stored in the storage section 82 in advance, the size corresponding to the imaging target received from the user, and sets the read size on the rotation controller 70. Alternatively, in step S1, the processing section 81 may calculate the size of an imaging target on the basis of an image taken by the imaging device 60 in advance, and may set the calculated size on the rotation controller 70.

In step S2, the processing section 81 receives the size of the field of view that is inputted by the user through the input section 84, and sets the received size of the field of view on the rotation controller 70. The size of the field of view changes depending on the magnification of the object lens 51 in the condensing optical system 50, the number of pixels of the imaging device 60, etc.

In step S2, the processing section 81 may cause the display section 83 to display a list of object lenses 51 and a list of imaging devices 60, and may receive an object lens 51 and an imaging device 60 that are selected by the user through the input section 84. In this case, the processing section 81 may read, from a mapping table stored in the storage section 82 in advance, the magnification of the object lens 51 received from the user and the number of pixels of the imaging device 60 received from the user. Then, the processing section 81 may calculate the size of the field of view on the basis of the magnification and the number of pixels, which have been read, and set the calculated size of the field of view on the rotation controller 70.

In step S3, the rotation controller 70 puts the size of the imaging target and the size of the field of view, which have been set by the processing section 81, into the above formula (2), thereby calculating the inclination angle θ of the light sheet 11. The processing section 81 may calculate the inclination angle θ of the light sheet 11 and transmit the calculated angle θ to the rotation controller 70.

In step S4, the rotation controller 70 causes the rotation mechanism section 32 to rotate the optical lens 31 such that the inclination of the light sheet 11 becomes the angle θ that is calculated in step S3. Thus, the inclination of the light sheet 11 is set such that all the cross-sectional images of the imaging target can be obtained and a high-definition image with reduced background noise can be taken.

The rotation controller 70 is not necessarily provided, and may be omitted. In this case, for example, an operator manually rotates the rotation mechanism section 32 such that the angle of the optical lens 31 becomes θ. Instead of the rotation mechanism section 32, a plurality of holders each having an optical lens 31 fixed thereto may be prepared so as to correspond to a plurality of angles of the optical lens 31. In this case, when an angle θ is calculated, a holder corresponding to the calculated angle θ is selected, and the selected holder is placed in the apparatus, whereby the angle of the optical lens 31 is changed. Arrangement of the holder may be performed manually or automatically.

Next, a process of generating a three-dimensional image is described.

Figure 15:
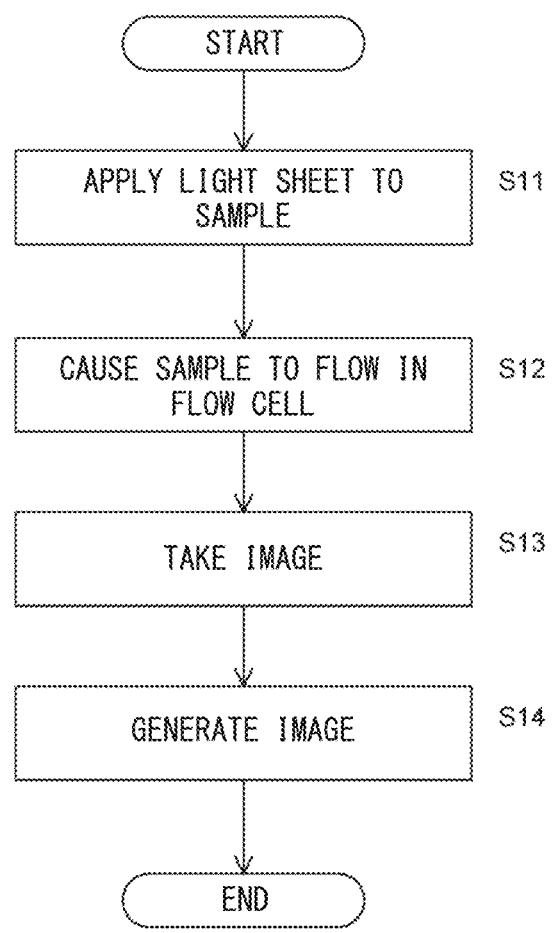
FIG. 15 is a flowchart showing process steps for generating a three-dimensional image according to Embodiment 1.

As shown in FIG. 15, in step S11, the user causes the light source 20 to emit light, thereby applying the light sheet 11 to a sample. The light source 20 may be connected to the interface 85. In this case, in step S11, the processing section 81 controls the light source 20 to apply the light sheet 11 to the sample.

In step S12, the user causes the sample containing a plurality of cells to flow in the flow path 41 of the flow cell 40. The sample is prepared such that the plurality of cells simultaneously cross the light sheet 11. The imaging unit 10a may include: a storage section for storing therein the prepared sample; and a transfer section for transferring the sample stored in the storage section to the flow cell 40. In this case, in step S11, the processing section 81 controls the transfer section of the cell imaging apparatus 10 so that the sample stored in the storage section flows in the flow cell 40.

In step S13, the processing section 81 causes the imaging device 60 to take images of fluorescences generated from nuclei 12a in the plurality of cells 12. Specifically, the images of the fluorescences are sequentially taken on the basis of the frame rate of the imaging device 60, and the taken images are sequentially stored in the storage section 82. In step S14, the processing section 81 generates an image including three-dimensional images of the plurality of cells, on the basis of the plurality of images taken by the imaging device 60. In step S14, a process shown in FIG. 16 is performed.

In step S21, the processing section 81 subjects the plurality of images taken by the imaging device 60 to distortion correction as described with reference to FIGS. 11A and 11B. Further, in steps S22 and S23, the processing section 81 subjects the plurality of distortion-corrected images to aspect-ratio correction and position adjustment as described with reference to FIG. 8 and FIG. 12A. That is, regarding a plurality of distortion-corrected images obtained from one nucleus 12a, the processing section 81 calculates the amount of movement of the nucleus 12a on the imaging surface 61 on the basis of the above formula (1), thereby performing aspect-ratio correction. In step S24, the processing section 81 performs superposition of the images as described with reference to FIG. 12B, on the basis of the calculated amount of movement, and the aspect-ratio-corrected images. Thus, the processing section 81 generates an image including the three-dimensional images of the plurality of nuclei 12a.

Figure 16:
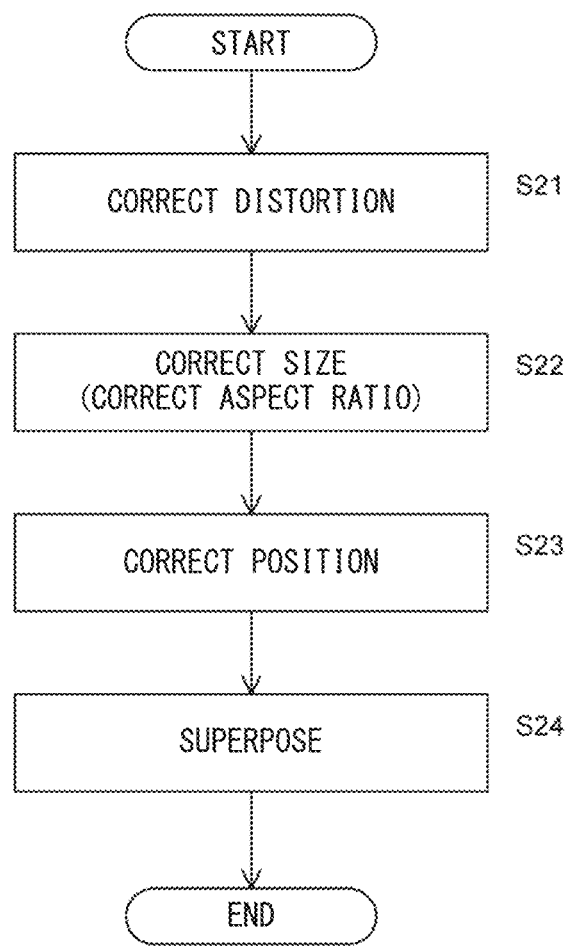
FIG. 16 is a flowchart showing the content of an image generation process according to Embodiment 1.
Figure 17:
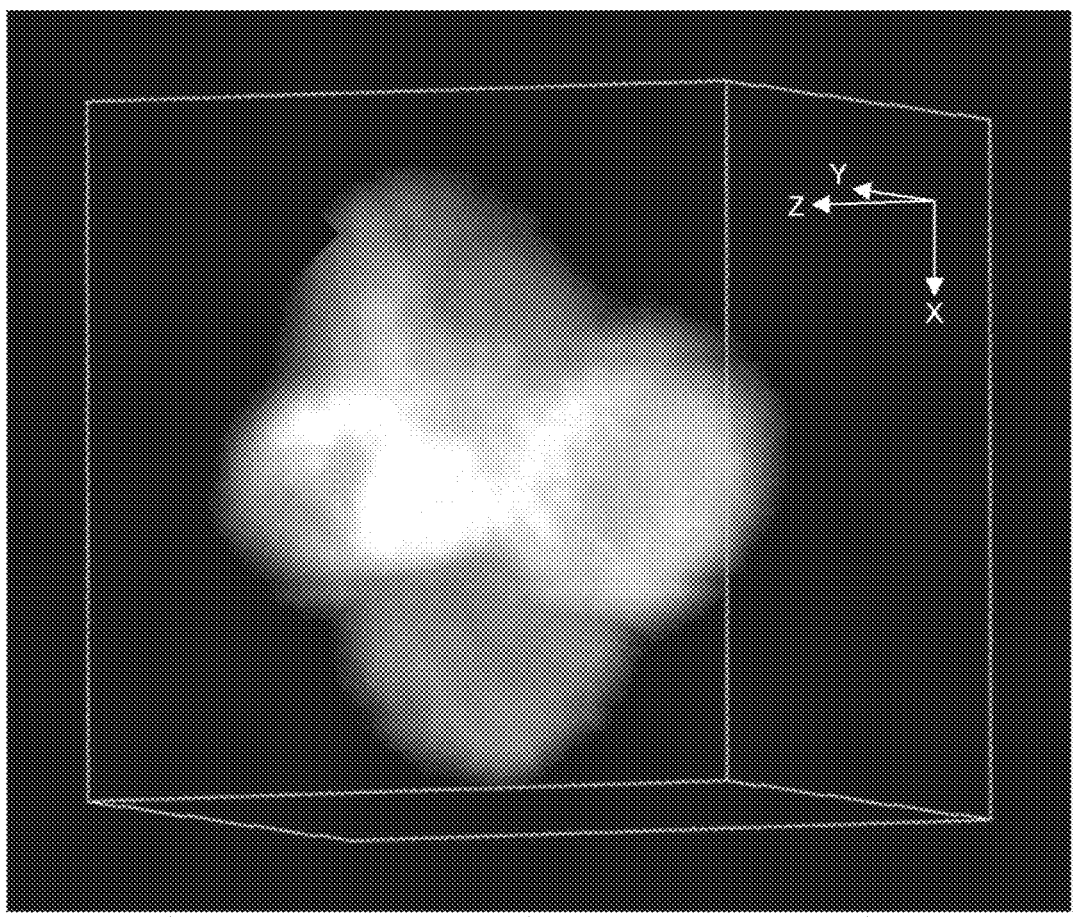
FIG. 17 is a diagram showing an example of a three-dimensional image in which a plurality of cells are aggregated, according to Embodiment 1.

If an aggregate of a plurality of cells crosses the light sheet 11, for example, a three-dimensional image as shown in FIG. 17 may be obtained through the processes shown in FIG. 15 and FIG. 16. In FIG. 17, an image including three-dimensional images of four nuclei 12a is obtained.

Embodiment 2

In the condensing optical system 50 according to Embodiment 2, the phase modulation element 55 is replaced with a phase modulation element that forms a double-helix PSF.

The "double-helix PSF" is a kind of a spiral point spread function, and is a point spread function that allows light generated from one bright point to be imaged onto two focal points. In Embodiment 2, the phase modulation pattern shown in FIG. 5A is replaced with a phase modulation pattern that forms a double-helix PSF. Other components of Embodiment 2 are identical to those of Embodiment 1.

Figure 18:
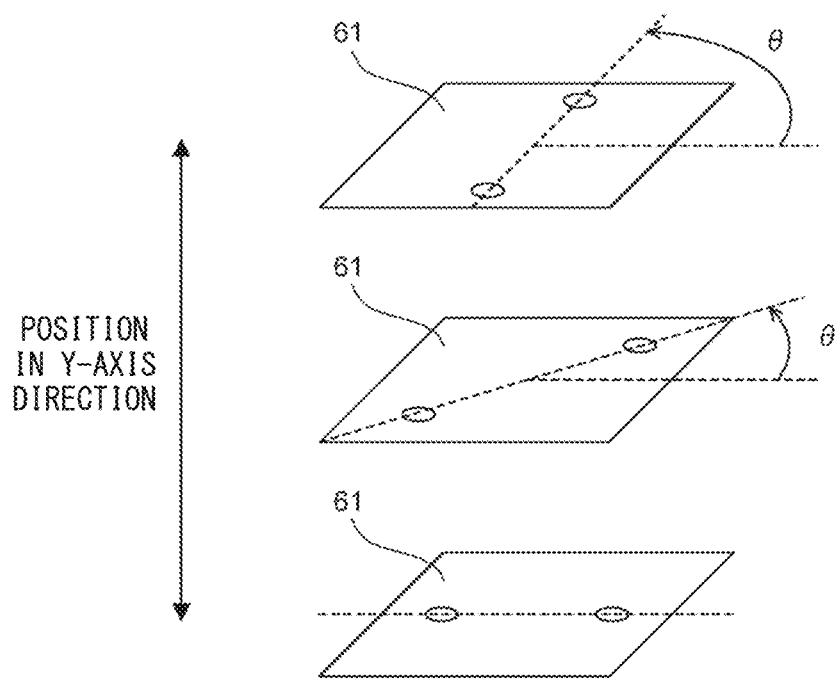
FIG. 18 is a diagram explaining an effect of a phase modulation element according to Embodiment 2.

As shown in FIG. 18, fluorescences generated from points at different positions in the Y-axis direction are imaged onto two focal points on the imaging surface 61 of the imaging device 60. At this time, the two focal points rotate on the imaging surface 61 in accordance with the positions of the bright points of the fluorescences in the Y-axis direction. That is, an angle formed by a reference line and a line connecting the two focal points changes on the imaging surface 61 in accordance with the positions of the bright points of the fluorescences in the Y-axis direction.

Figure 19:
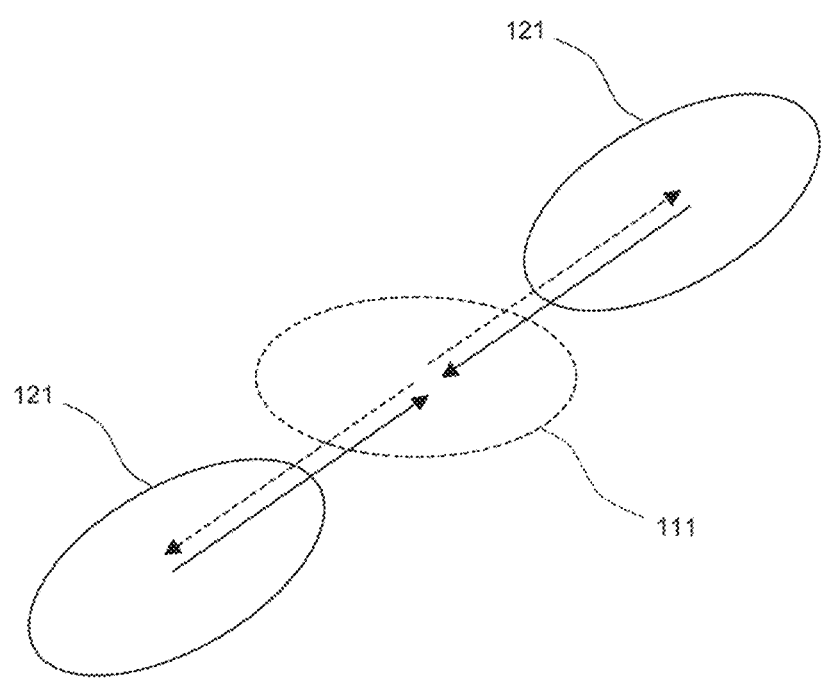
FIG. 19 is a diagram explaining a cross-sectional image correcting method according to Embodiment 2.
Figure 20A:
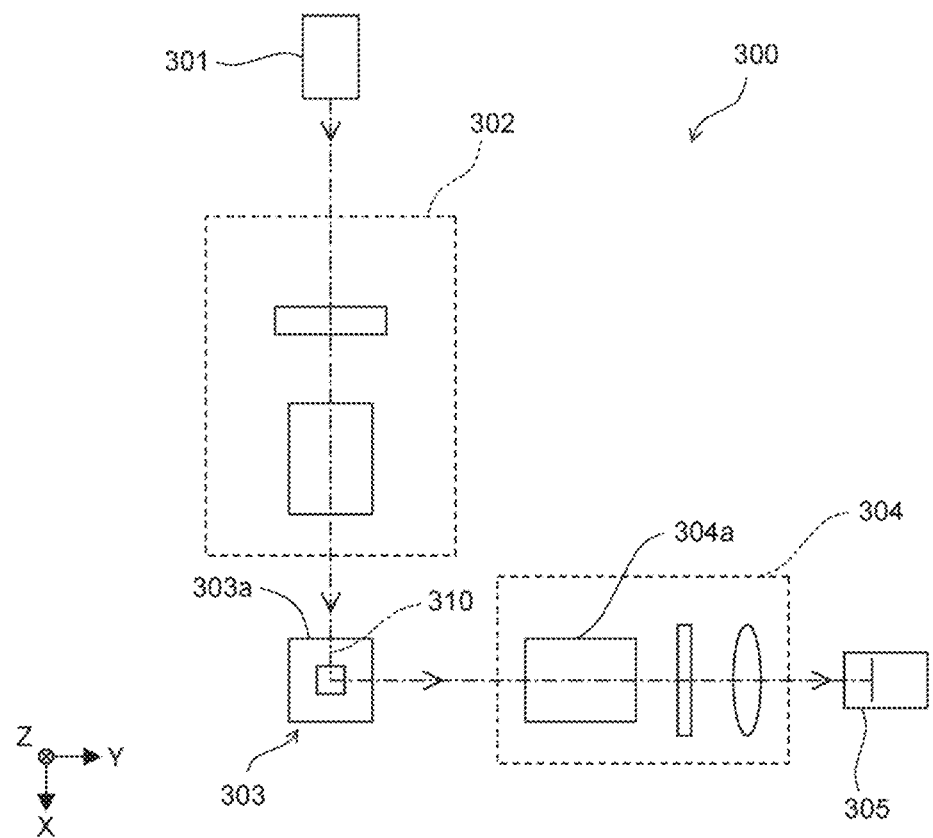
FIG. 20A is a diagram explaining the configuration of a related art.
Figure 20B:
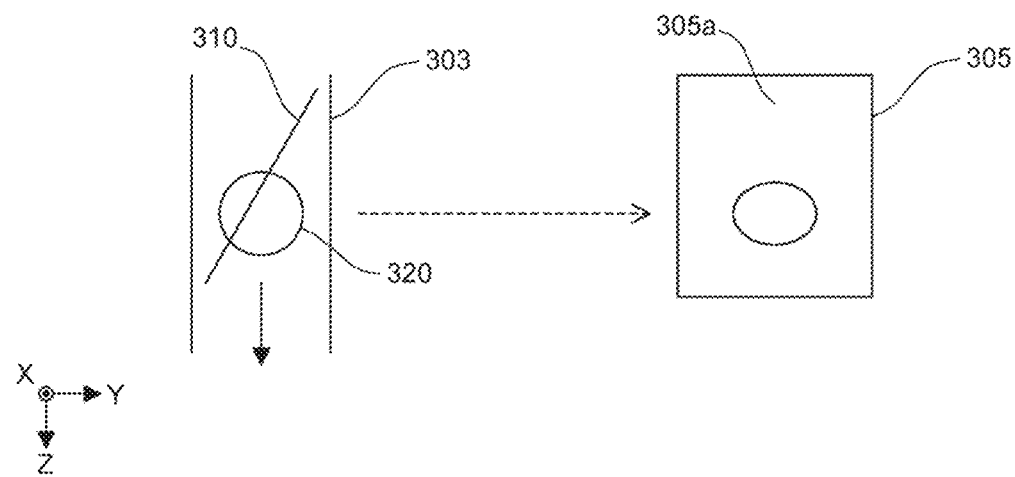
FIG. 20B is a diagram schematically showing portions corresponding to a flow cell and an imaging device in the configuration of the related art.

As shown in FIG. 19, in a case where the phase modulation element 55 is not provided, fluorescence generated from one bright point at a cell cross section is applied to the imaging surface 61 in the irradiation area 111. On the other hand, when the phase modulation element 55 that forms a double-helix PSF is provided, as shown in FIG. 19, fluorescence generated from one bright point at a cell cross section is applied to two irradiation areas 121. In this case, the fluorescence, which has been applied to an irradiation position P41 in the irradiation area 111 when the phase modulation element 55 is not provided, is split into two beams to be applied to irradiation positions P42 in the two irradiation areas 121.

Therefore, when the phase modulation element 55 that forms a double-helix PSF is used, the image elements obtained from the two irradiation areas 121 can be shifted to the irradiation area 111 by using, as correction vectors, vectors that are opposite to the vectors respectively directed to the two irradiation areas 121 from the irradiation area 111, i.e., vectors indicated by solid lines in FIG. 19.

In the distortion correction process, the processing section 81 searches the pixels on the imaging surface 61, to which the fluorescence is applied, for two pixels to be paired. For example, the processing section 81 selects pixel lines, one by one, from the uppermost pixel line. In each selected pixel line, the processing section 81 specifies a pixel to which the fluorescence is applied. Then, the processing section 81 specifies a pixel in another pixel line, which is to be paired with the above specified pixel, on the basis of the positional relationship of the two focal points shown in FIG. 18, and if the fluorescence is applied to this pixel, the processing section 81 obtains these two pixels as pixels to be paired. As shown in FIG. 18, the positional relationship between the two focal points differs per selected pixel line, that is, differs according to the distance between the imaging surface and the bright point of the fluorescence. Therefore, each pixel in each pixel line is associated with another pixel in another pixel line to be paired therewith due to the effect of the double-helix PSF. On the basis of the association relationship, the processing section 81 obtains two images to which the fluorescence is applied, as two pixels to be paired. Thus, the processing section 81 obtains pixels to be paired, from all the pixels in all the pixel lines.

Thereafter, the processing section 81 superposes the image elements obtained from the pair of pixels onto an intermediate pixel position between these pixels. The processing section 81 performs this process for all the pairs of pixels. Thus, all the pairs of image elements obtained from the cell cross section are superposed on one another. Thus, the processing section 81 obtains the distortion-corrected cross-sectional image of the cell. The process after the distortion correction is the same as that of Embodiment 1.

Also by the configuration of Embodiment 2, a distortion-corrected cross-sectional image can be obtained. Therefore, a high-quality cell image can be obtained as in Embodiment 1.

In the configuration of Embodiment 2, however, since the fluorescence generated from one bright point is split into two beams to be applied to the imaging surface 61, fluorescences generated from the cross section of the cell needs to be separated on the imaging surface 61 so that pairs of image elements obtained from the pixels on the imaging surface 61 can be specified. Embodiment 2 is applicable to a cell that allows separation of fluorescences in the above-described manner. For example, when the size of each cell is small and the density of cells flowing in the flow cell 40 is low, fluorescences at the bright points generated from the cross section of the cell are separated on the imaging surface 61 so that the pairs can be specified. The configuration of Embodiment 2 is applicable to such a case.

In contrast to Embodiment 2, since the phase modulation element 55 that forms the single-helix PSF is used in Embodiment 1, fluorescences generated from the portions at the cell cross section are not separated. Therefore, for any cell, distortion that occurs in a taken image can be smoothly corrected.

For only one of the two irradiation areas 121 shown in FIG. 19, the image element thereof may be shifted by the correction vector to obtain a distortion-corrected cross-sectional image. In this case, however, the distortion-corrected cross-sectional image is darker than that obtain in the case where the image elements of the two irradiation areas 121 are superposed. In Embodiment 2, a bright cross-sectional image can be obtained by superposing the paired image elements.

As for the phase modulation element 55, a phase modulation element that forms a multi-helix PSF equal to or more than triple-helix may be used. The "multi-helix PSF" is a kind of a spiral point spread function, and is a point spread function that allows light generated from one bright point to be imaged onto a plurality of focal points. Also in this case, paired image elements may be superposed on an intermediate position between the image elements. Thus, a bright cross-sectional image can be obtained. For example, when a phase modulation element that forms a triple or more helix PSF is used as the phase modulation element 55, a set of three image elements may be interposed on an intermediate position among the three image elements, i.e., a center-of-gravity position among the three image elements.

While in Embodiments 1 and 2, light to be imaged by the imaging device 60 is fluorescence, light to be imaged by the imaging device 60 may be light that is generated on the side of the flow cell 40 from a cell as an imaging target, for example, side scattered light.

While in Embodiments 1 and 2, the flow cell 40 has a square outer shape as viewed in the Z-axis direction, the flow cell 40 may have a circular outer shape as viewed in the Z-axis direction. For example, when the flow cell 40 is formed in a columnar shape, the flow cell 40 has a circular outer shape as viewed in the Z-axis direction, and the outer side surface of the flow cell 40 is a curved surface. When the flow cell 40 is formed in a columnar shape, the light sheet 11 is perpendicular to the tangential plane of the outer side surface of the flow cell 40. In this case, the light sheet 11 incident on the flow cell 40 is inhibited from being deflected by the outer side surface, whereby the shape of the light sheet 11 applied to the cell 12 is less likely to be deformed. Accordingly, the imaging device 60 is allowed to take a high-definition image.

Modifications

In Embodiments 1 and 2, description has been given of the configuration in which a plurality of cells are simultaneously imaged. However, it is possible to extract an invention regarding distortion correction for a taken image. In this case, a plurality of cells are not necessarily imaged simultaneously. A sample may be caused to flow in the flow cell 40 such that only one cell crosses the light sheet 11.

Particles to be imaged are not limited to cells, and may be particles other than cells. For examples, particles to be imaged may be organism-derived particles other than cells, light-transmitting particles such as fluorescence beads, or the like. That is, any particles may be used as long as the particles have light translucency and generate light to the outside of the flow cell when being irradiated with light. Further, fluorescence images of HER2 gene and CEP17 as a centromere region of chromosome 17 may be obtained as well as the fluorescence image of the nucleus 12a. Besides, fluorescence images of other portions in a cell, such as other genes, nucleus acids, cytoplasm, protein, organelle, etc., may be obtained.

A particle imaging apparatus according to this modification may have the same configuration as the configurations of the cell imaging apparatuses 10 according to Embodiments 1 and 2. A particle imaging method according to this modification may be the same as the processes shown in FIGS. 15 and 16 of Embodiments 1 and 2. In this modification, distortion correction for taken images may be performed in the same manner as step S21 of Embodiments 1 and 2. In addition, the processes in steps S22 and S23 in FIG. 16 are also performed in the same manner.

When HER2 gene and CEP17 are imaging targets as well as the nucleus 12a, fluorescences generated from the HER2 gene and the CEP17 are projected as bright points in the irradiation area of the nucleus 12a, and therefore, the HER2 gene and the CEP17 are also included in the cross-sectional image of the nucleus 12a. Further, according to the distortion correction, aspect-ratio correction, and position adjustment as described above, the HER2 gene and the CEP17 are also subjected to distortion correction, aspect-ratio correction, and position adjustment. Therefore, in this modification, the bright points of the HER2 gene and the CEP17 are included in a three-dimensional image, of the nucleus 12a, formed by superposing the cross-sectional images of the nucleus 12a. Thus, according to this modification, regarding not only a portion having a certain size, such as the nucleus 12a, but also fine portions such as the HER2 gene and the CEP17, a three-dimensional image in which three-dimensional distribution states of these portions are reflected can be obtained on the basis of a plurality of images taken by the imaging device 60.

The element (55) for extending the depth of focus is not limited to a phase modulation element, and a variable focal point lens may be used to extend the depth of focus.

What is claimed is:

1. A cell imaging method comprising:
   forming a light sheet having a flat sheet surface in a flow path of a flow cell;
   flowing a measurement sample containing a plurality of cells in the flow cell and through the light sheet;
   directing light generated from the plurality of cells passing through the light sheet to an imaging device via an optical system, the optical system including an objective lens and an element configured to extend a depth of focus of the imaging device, the element located between the objective lens and the imaging device in a light path; and
   taking images of the plurality of cells with the imaging device,
   wherein the light sheet is formed such that the flat sheet surface is not perpendicular or parallel to a flow direction of the sample and the distance between the flat sheet surface and the optical system is not constant along the flow direction; and
   correcting distortion of the taken image by:
      shifting first image elements corresponding to a first line of pixels of the imaging device in a first direction and by a first distance; and
      shifting second image elements corresponding to a second line of pixels of the imaging device in a second direction and by a second distance,
   wherein the first line of pixels are in a same distance from the light sheet and the second line of pixels are in a same distance from the light sheet, and
   the element is a phase modulation element configured to modulate a phase of light from the plurality of cells passing through the light sheet according to a single-helix point spread function.

2. The cell imaging method of claim 1, wherein the plurality of cells are caused to simultaneously pass through the light sheet, and lights generated from the plurality of cells are received by the imaging device.

3. The cell imaging method of claim 1, wherein the point spread function is a spiral point spread function.

4. The cell imaging method of claim 1, wherein the distortion is caused by the phase modulation element.

5. The cell imaging method of claim 4, wherein in the correcting of the distortion of the taken image, the first image elements and the second image elements are each shifted to a position at which displacement thereof based on the point spread function is corrected.

6. The cell imaging method of claim 5, wherein the first distance is between the light sheet and a position, on an imaging surface, at which the first image elements are obtained.

7. The cell imaging method of claim 6, wherein the first direction and the first distance are based on the first distance between the light sheet and the position, on the imaging surface, at which the image elements are obtained.

8. The cell imaging method of claim 5, wherein each image element of the first image elements is an image element obtained pixel by pixel.

9. The cell imaging method of claim 1, further comprising:
   taking a plurality of images each including a plurality of cells; and
   generating an image including three-dimensional images of the plurality of cells on the basis of the plurality of taken images.

10. The cell imaging method of claim 9, wherein:
    the generating of the image includes correcting a position of the image of each cell at the imaging surface, and
    in the correcting of the position, an amount of shifting of the image of the cell on the imaging surface is calculated on the basis of, at least, an amount of movement of the cell in the flow cell, and an angle of the light sheet with respect to a flow direction of the sample, and the three-dimensional image of the cell is generated on the basis of the calculated amount of shifting, and a series of the taken images obtained along with movement of the cell.

11. The cell imaging method of claim 9, wherein:
the generating of the image includes correcting a size of the image of each cell on the imaging surface, and
in the correcting of the size, the size of the taken image of the cell is corrected on the basis of an angle of the light sheet with respect to a flow direction of the sample, and
the three-dimensional image of the cell is generated on the basis of the size-corrected image.

12. A cell imaging apparatus comprising:
a flow cell configured to cause a sample containing a plurality of cells to flow therein;
a light source;
an irradiation optical system configured to form, with respect to the flow cell, a light sheet having a flat sheet surface from light emitted from the light source;
a condensing optical system having an objective lens and an element configured to extend a depth of focus, the condensing optical system being configured to condense light generated from the plurality of cells flowing in the flow cell;
an imaging device configured to receive light generated from the plurality of cells and condensed by the condensing optical system, and take images of the plurality of cells,
   wherein the light sheet is such that the flat sheet surface is not perpendicular or parallel to a flow direction of the sample and a distance between the flat sheet surface and the condensing optical system is not constant along the flow direction, and
   wherein the element is a phase modulation element configured to modulate a phase of light from the plurality of cells passing through the light sheet according to a single-helix point spread function; and
at least one processor configured to correct distortion of at least one of the images by:
   shifting first image elements corresponding to a first line of pixels of the imaging device in a first direction and by a first distance; and
   shifting second image elements corresponding to a second line of pixels of the imaging device in a second direction and by a second distance,
   wherein the first line of pixels are in a same distance from the light sheet and the second line of pixels are in a same distance from the light sheet.

13. The cell imaging apparatus of claim 12, wherein the phase modulation element forms a spiral point spread function at an imaging surface of the imaging device.

14. The cell imaging apparatus of claim 13, wherein the spiral point spread function is a single-helix point spread function.

15. A particle imaging method comprising:
forming a light sheet having a flat sheet surface with respect to a flow cell facing to the flat sheet surface;
taking an image of light generated from a particle that flows in the flow cell, via a phase modulation element configured to modulate a point spread function; and
correcting distortion of the taken image, the distortion being caused by the phase modulation element, the correcting distortion comprising:
   shifting first image elements corresponding to a first line of pixels of the imaging device in a first direction and by a first distance; and
   shifting second image elements corresponding to a second line of pixels of the imaging device in a second direction and by a second distance,
   wherein the first line of pixels are in a same distance from the light sheet and the second line of pixels are in a same distance from the light sheet, and
wherein the point spread function is a single-helix point spread function.

* * * * *